United States Patent [19]
Starke

[11] Patent Number: 5,889,021
[45] Date of Patent: Mar. 30, 1999

[54] ACTIVE COMPOUNDS

[75] Inventor: Carl Ingemar Starke, Göteborg, Sweden

[73] Assignee: Astra Aktiebolag, Sodertalje, Sweden

[21] Appl. No.: 270,167

[22] PCT Filed: Jun. 8, 1994

[86] PCT No.: PCT/SE94/00552

§ 371 Date: Jul. 1, 1994

§ 102(e) Date: Jul. 1, 1994

[87] PCT Pub. No.: WO94/29274

PCT Pub. Date: Dec. 22, 1994

[30] Foreign Application Priority Data

Jun. 11, 1993 [SE] Sweden ................................. 9302005
Nov. 30, 1993 [SE] Sweden ................................. 9303970

[51] Int. Cl.$^6$ ........................ A61K 31/47; C07D 215/38;
C07D 215/44; C07D 215/14

[52] U.S. Cl. ........................ 514/313; 514/311; 546/160; 546/161; 546/168

[58] Field of Search .................... 546/160, 161, 546/168; 514/313, 311

[56] References Cited

U.S. PATENT DOCUMENTS

| | | | |
|---|---|---|---|
| 3,470,186 | 9/1969 | Hanifin | 514/313 |
| 4,011,332 | 3/1977 | Schoetensack et al. | 424/273 |
| 4,042,702 | 8/1977 | Rainer et al. | 424/273 |
| 4,093,812 | 6/1978 | Rainer et al. | 548/374 |
| 4,120,966 | 10/1978 | Brown et al. | 424/263 |
| 4,239,901 | 12/1980 | Rainer et al. | 560/34 |
| 4,243,678 | 1/1981 | Krastinat et al. | 424/319 |
| 4,250,183 | 2/1981 | Krastinat et al. | 424/263 |
| 4,272,507 | 6/1981 | Figala et al. | 424/275 |
| 4,317,823 | 3/1982 | Rainer et al. | 424/248.54 |
| 4,324,796 | 4/1982 | Eistetter et al. | 424/278 |
| 4,334,089 | 6/1982 | Kraas et al. | 562/463 |
| 4,337,267 | 6/1982 | Eistetter et al. | 424/278 |
| 4,343,804 | 8/1982 | Munson | 546/159 |
| 4,363,816 | 12/1982 | Senn-Bilfinger | 424/274 |
| 4,381,301 | 4/1983 | Rainer et al. | 424/250 |
| 4,395,414 | 7/1983 | Eistetter et al. | 424/258 |
| 4,430,339 | 2/1984 | Eistetter et al. | 424/278 |
| 4,578,381 | 3/1986 | Uchida et al. | 514/233 |
| 4,738,970 | 4/1988 | Uchida et al. | 514/312 |
| 4,806,549 | 2/1989 | Ife | 514/313 |
| 4,935,431 | 6/1990 | Ife et al. | 514/301 |
| 5,006,535 | 4/1991 | Ife et al. | 514/313 |
| 5,049,567 | 9/1991 | Ife et al. | 514/313 |
| 5,051,508 | 9/1991 | Brown et al. | 546/84 |
| 5,064,833 | 11/1991 | Ife et al. | 514/260 |
| 5,082,841 | 1/1992 | Brown | 514/235.2 |
| 5,082,848 | 1/1992 | Ife | 514/313 |
| 5,089,498 | 2/1992 | Ife et al. | 514/235.2 |
| 5,102,892 | 4/1992 | Geiss et al. | 514/313 |
| 5,143,920 | 9/1992 | Ife et al. | 514/313 |
| 5,200,417 | 4/1993 | Brown et al. | 546/310 |
| 5,215,999 | 6/1993 | Uchida et al. | 514/313 |
| 5,250,527 | 10/1993 | Ife et al. | 514/234.5 |

FOREIGN PATENT DOCUMENTS

| | | |
|---|---|---|
| 0259174 | 4/1987 | European Pat. Off. . |
| 0330485 | 2/1989 | European Pat. Off. . |
| 0399267 | 5/1990 | European Pat. Off. . |
| 0416749 | 6/1990 | European Pat. Off. . |
| 0 399 267 | 11/1990 | European Pat. Off. . |
| 9212969 | 1/1992 | WIPO . |
| 9312090 | 12/1992 | WIPO . |

OTHER PUBLICATIONS

C.A. Leach et al. "Reversible in inhibitors of the gastric (H+/K+) –AT Pase." Med. Chem. 1995, 38, 2748–62.

R.J. Ife et al. "SAR of 3–Acryl–4–(Arylamine) quinolines . . ." 5th Cypress conference New Meth, May, 1992 and poster.

*Primary Examiner*—Margaret M. Mach
*Attorney, Agent, or Firm*—White & Case LLP

[57] ABSTRACT

The present invention relates to novel quinoline derivatives of the formula

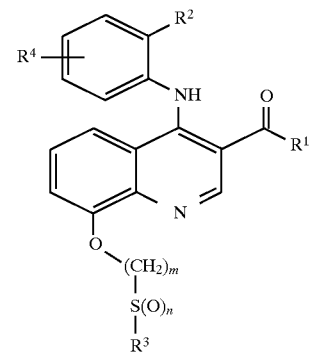

which inhibit exogenously or endogenously stimulated gastric acid secretion and thus can be used in the prevention and treatment of gastrointestinal inflammatory diseases.

10 Claims, No Drawings

ACTIVE COMPOUNDS

This application is a 371 of PCT/SE94/00552, filed Jun. 8, 1994.

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Substituted quinoline derivatives that inhibit gastric acid secretion are known in the art, for example from EP-A1–259,174 and EP-A1–330,485.

DISCLOSURE OF THE INVENTION

It has surprisingly been found that compounds of the formula I, which are 4-amino-3-acylquinoline derivatives in which the quinoline is substituted in the 8-position by alkylthioethoxy, alkylthiopropoxy, alkylsulfinylethoxy, alkylsulfinylpropoxy, alkylsulfonylethoxy or alkylsulfonylpropoxy, are effective as inhibitors of gastric acid secretion, and that they exert this effect by inhibiting the gastrointestinal $H^+,K^+$-ATPase.

In one aspect, the invention thus relates to compounds of the general formula I:

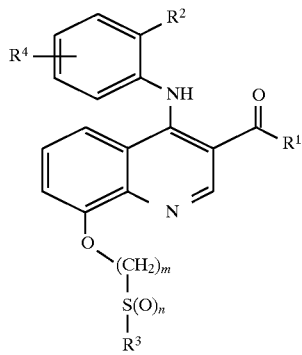

I or a pharmaceutically acceptable salt thereof, wherein $R^1$ is
(a) $C_1$–$C_6$ alkyl,
(b) $C_3$–$C_6$ cykloalkyl, or
(c) $C_3$–$C_6$, $C_1$–$C_6$ cykloalkylalkyl;

$R^2$ is
(a) H,
(b) $C_1$–$C_6$ alkyl,
(c) $C_1$–$C_6$ alkoxy, or
(d) halogen;

$R^3$ is $C_1$–$C_6$ alkyl;

$R^4$ is
(a) H,
(b) $C_1$–$C_4$ alkyl,
(c) halogen, or
(d) OH;

m is an integer 2 or 3; and n is an integer 0, 1 or 2.

Throughout the specification and the appended claims, a given chemical formula or name shall encompass all stereo and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "$C_1$–$C_6$ alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl.

Unless otherwise stated or indicated, the term "cycloalkyl" denotes a cyclic alkyl group having a ring size from $C_3$ to $C_6$, optionally additionally substituted by lower alkyl. Examples of said cycloalkyl include cyclopropyl, cyclobutyl, cyclopentyl, cyclohexyl, methylcyclohexyl and cydoheptyl.

Unless otherwise stated or indicated, the term "$C_1$–$C_6$ alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "halogen" shall mean fluorine, chlorine, bromine or iodine.

Depending on the process conditions and the starting materials, the end products of the formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids, sulfonic acids, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid or naphthalenesulfonic acid.

Preferred compounds of the formula I are those wherein $R^1$ is $CH_3$, $CH_2CH_3$, $CH_2CH_2CH_3$, $CH(CH_3)_2$, cyclopropyl or cyclopropylmethyl;

$R^2$ is $CH_3$, $CH_2CH_3$, $CH_2CH_2CH_3$, $CH(CH_3)_2$, $CH(CH_3)CH_2CH_3$, $OCH_3$, $OCH_2CH_3$, or halogen;

$R^3$ is $CH_3$, $CH_2CH_3$, $CH(CH_3)_2$ or $CH_2CH_2CH_3$; and $R^4$ is H, $CH_3$, $CH_2CH_3$, halogen or OH.

More preferred compounds of the formula I are those wherein $R^1$ is $CH_2CH_3$ or $CH_2CH_2CH_3$;

$R^2$ is $CH_3$, $CH_2CH_3$, $CH(CH_3)_2$, $OCH_3$, or Cl;

$R^3$ is $CH_3$, $CH_2CH_3$ or $CH_2CH_2CH_3$; and $R^4$ is H, $CH_3$, F. Cl or OH.

The most preferred compound of the invention is that wherein $R^1$ is $CH_2CH_2CH_3$, $R^2$ and $R^3$ is $CH_3$; $R^4$ is H; m is 2; and n is 1; i.e. the compound 3-butyryl-4-(2-methylphenylamino)-8-(2-methylsulfinylethoxy)quinoline.

In a further aspect, the invention relates to compounds of the formula I for use in therapy.

Preparation

The present invention also provides processes for the manufacture of the compounds with the general formula I. Such compounds are prepared in the following way:

(A) A compound of the general formula II

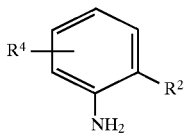

wherein $R^2$ and $R^4$ are as defined above is reacted with a compound of the general formula III

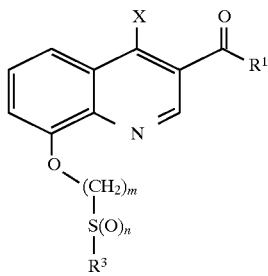

wherein $R^1$, $R^3$, m and n are as defined above and X is a leaving group, such as a halide, tosyloxy or mesyloxy.

Compounds of formula III are novel and represent as such a further aspect of the invention.

This reaction is conducted with or without a solvent. When a solvent is used, it is preferably a solvent such as acetonitrile, tetrahydrofuran, toluene or dimethyl formamide.

When the reaction is conducted with a solvent, the reaction temperature usually ranges from about 20° C. to about the boiling point of the solvent used, more preferably from about 20° C. to about 110° C. The reaction time usually ranges from about 1 hour to about 24 hours.

When the reaction is conducted without a solvent, the reaction temperature usually ranges from about 30° C. to about 170° C. The reaction time usually ranges from 15 minutes to about 2 hours.

(B) Compounds of the formula I wherein $R^1$, $R^2$, $R^3$, $R^4$ and m are as defined above under (A) and n is 1 or 2 can be prepared by oxidizing a compound of formula I wherein $R^1$, $R^2$, $R^3$, $R^4$ and m are as defined above under (A) and n is 0.

This oxidation may be carried out by using an oxidizing agent such as sodium hypochlorite, nitric acid, hydrogen peroxide, (optionally in presence of vanadium compounds), peracids, peresters, ozone, dinitrogentetraoxide, iodosobensene, N-halosuccinimide, 1-chlorobensotriazole, t-butylhypochlorite, diazabicyclo-[2,2,2]-octane bromine complex, sodium metaperiodate, selenium dioxide, manganese dioxide, chromic acid, cericammonium nitrate, bromine, chlorine, and sulfuryl chloride. The oxidation takes place in a solvent such as halogenated hydrocarbons, alcohols, ethers or ketones.

The oxidation may also be carried out enzymatically by using an oxidizing enzyme or microbiotically by using a suitable microorganism.

Compounds of the general formula II are commercially available or can be prepared by known methods.

Compounds of the general formula III can be prepared according to known methods and according to the Examples below.

Use

In a further aspect, the invention relates to the use of a compound as defined above for the manufacture of a medicament for the inhibition of gastric acid secretion, or for the treatment of gastrointestinal inflammatory diseases.

In a more general sense, the compounds of the invention may be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrom.

Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre-and postoperatively to prevent acid aspiration and stress ulceration.

Pharmaceutical formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. for the treatment or prophylaxis of conditions involving infection by *Helicobacter pylori* of human gastric mucosa. Such other active ingredients may be antimicrobial agents, especially:

β-lactam antibiotics such as amoxicillin, ampicillin, cephalothin, cefaclor or cefixime; or macrolides such as erythromycin, or clarithromycin; or tetracyclines such as tetracycline or doxycycline; or aminoglycosides such as gentamycin, kanamycin or amikacin; or quinolones such as norfloxacin, ciprofloxacin or enoxacin; or others such as metronidazole, nitrofurantoin or chloramphenicol;

or preparations containing bismuth salts such as bismuth subcitrate, bismuth subsalicylate, bismuth subcarbonate, bismuth subnitrate or bismuth subgallate.

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.2–20% by weight in preparations for parenteral use and preferably between 1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium steryl fumarate and polyethylene glycol waxes. The mixture is then processed into granules or pressed into tablets. Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

EXAMPLES

1. PREPARATION OF COMPOUNDS OF THE INVENTION

Example 1
Preparation of 3-butyryl-4-(2-methylphenylamino)-8-(2-methylthioethoxy)quinoline A mixture of 3-butyryl-4-chloro-8-(2-methylthioethoxy) quinoline (0.67 g, 2.1 mmol) and o-toluidine (0.24 g, 2.3 mmol) in acetonitrile was heated to 55° C. and stirred for 3.5 h. The solvent was evaporated and the residue was partitioned between methylene chloride and a saturated sodium bicarbonate solution. The organic layer was dried over sodium sulfate and evaporated. The residue was triturated with diisopropylether. The precipitated product was filtered off and washed with diisopropyl ether giving 0.55 g (66%) of the title compound.

($^1$H-NMR, 500 MHz, CDCl$_3$) 1.05 (t,3H), 1.84 (m,2H), 2.25 (s,3H), 2.35 (s,3H), 3.10 (m,4H), 4.34 (t,2H), 6.89 (d,1H), 6.95–7.15 (m,5H), 7.27 (d,1H), 9.26 (s,1H), 11.84 (s,1H).

Example 2
Preparation of 3-butyryl-4-(2-methylphenylamino)-8-(2-methylsulfinylethoxy)quinoline 3-Butyryl-4-(2-methylphenylamino)-8-(2-methylthioethoxy)quinoline (0.15 g, 0.38 mmol) was dissolved in methylene chloride (3 ml) and cooled to –20° C. A solution of 71% m-CPBA (0.089 g, 0.36 mmol) in 1 ml of methylene chloride was added dropwise. The temperature was allowed to rise to room temperature whereafter the solution was stirred for 15 min at room temperature. The reaction mixture was washed with a saturated sodium bicarbonate solution. The organic layer was dried over sodium sulfate and evaporated. Chromatography with methylene chloride:methanol 10:1 as the eluent gave 0.064 g (41%) of the desired product.

($^1$H-NMR, 300 MHz, CDCl$_3$) 1.04 (t,3H), 1.82 (m,2H), 2.34 (s,3H), 2.80 (s,3H), 3.08 (t,2H), 3.21 (m,1H), 3.44 (m,1H), 4.62 (m,2H), 6.89 (d,1H), 6.94–7.16 (m,5H), 7.28 (d,1H), 9.20 (s,1H), 11.82 (s,1H).

Example 3
Preparation of 3-butyryl-4-(2-methylphenylamino)-8-(2-methylsulfonylethoxy)quinoline 3-Butyryl-4-(2-methylphenylamino)-8-(2-methylthioethoxy)quinoline (0.037 g, 0.092 mmol) was dissolved in methylene chloride (1.5 ml) and cooled to –20° C. A solution of 71% m-CPBA (0.047 g, 0.19 mmol) in 0.5 ml methylene chloride was added dropwise. The temperature was allowed to rise to room temperature whereafter the solution was stirred for 30 min at room temperature and the organic layer was washed with a saturated sodium bicarbonate solution. The organic layer was dried over sodium sulfate and evaporated. Trituration with diisopropyl ether and the product crystallized. After chromatography of the precipitate with methylene chloride:ethyl acetate 1:1 as the eluent, at the end pure ethyl acetate, 0.022 g (56%) of the title compound was isolated.

($^1$H-NMR, 500 MHz, CDCl$_3$) 1.07 (t,3H), 1.84 (m,2H), 2.35 (s,3H), 3.10 (t,2H), 3.39 (s,3H), 3.62 (t,2H), 4.61 (t,2H), 6.89 (d,1H), 6.94–7.17 (m,5H), 7.28 (m,1H), 9.15 (s,1H), 11.86 (s,1H).

Example 4
Preparation of 3-butyryl-4-(2-isopropylphenylamino)-8-(2-methylthioethoxy)quinoline A mixture of 3-butyryl-4-chloro-8-(2-methylthioethoxy) quinoline (400 mg, 1.23 mmol) and 2-isopropylaniline (1.0 g, 7.4 mmol) was heated to 150° C. for 30 min. The mixture was diluted with CHCl$_3$ and extracted with 2N HCl. The organic phase was washed with a saturated sodium bicarbonate solution. The organic layer was dried over Na$_2$SO$_4$ and evaporated. The residue was chromatographed (SiO$_2$; CH$_2$Cl$_2$:MeOH 95:5) yielding 340 mg (80.5%) of the desired product.

($^1$H-NMR, 300 MHz, CDCl$_3$): 1.0 (t,3H), 1.1 (d,3H), 1.2 (d,3H), 1.75 (m,2H), 2.15 (s,3H), 3.1 (m,3H), 3.2 (t,2H), 4.3 (t,2H), 6.8 (d,1H), 7.0–7.2 (m,4H), 7.4 (m,2H), 9.4 (d,1H).

Example 5
Preparation of 3-butyryl-4-(2-isopropylphenylamino)-8(2-methylsulfinylethoxy)quinoline.

3-Butyryl-4-(2-isopropylphenylamino)-8-(2-methylthioethoxy)quinoline (0.22 g, 0.52 mmol) was dissolved in methylene chloride (15 ml) and added to a mixture of 0.093g NaHCO$_3$ in 15 ml H$_2$O. A solution of 71% m-CPBA (0.12 g, 0.50 mmol) in 7 ml methylene chloride was added dropwise at 4° C. The solution was stirred for one hour at this temperature. The reaction mixture was washed with a saturated sodium bicarbonate solution. The organic layer was dried over $Na_2SO_4$ and evaporated. Chromatography with methylene chloride:methanol 10:1 as eluent gave 0.130 g (57%) of the desired product.

($^1$H-NMR, 300 MHz, $CDCl_3$). 1.0 (t,3H), 1.3 (m,6H), 1.8 (m,2H), 2.78 (s,3H), 3.08 (t,2H), 3.2 (m,6H), 3.35 (m,1H), 3.45 (m,1H), 4.6 (m,2H), 6.82 (d,1H), 6.86 (t,1H), 7.05 (m,3H), 7.2 (t,1H), 7.38 (d,1H), 9.18 (s,1H), 11.8 (s,1H).

Example 6
Preparation of 3-butyryl-4-(2-isopropylphenylamino)-8-(2-methylsulfonylethoxy)quinoline.

A mixture of 3-butyryl-4-(2-isopropylphenylamino)-8-(2-methylthioethoxy)quinoline (0.22 g, 0.52 mmol) in 15 ml methylene chloride and $NaHCO_3$ (0.186 g, 2.2 mmol) in 15 ml $H_2O$ was cooled to 4° C. A solution of 70% m-CPBA (0.24 g, 1.0 mmol) in 7 ml methylene chloride was added dropwise. After stirring for 1 h at 4° C., the organic layer was dried over $Na_2SO_4$ and evaporated. Chromatography ($SiO_2$; $CH_2Cl_2$:MeOH 90:10) gave 16 mg (6.8%) of the desired product.

($^1$H-NMR, 300 MHz, $CDCl_3$): 1.05 (t,3H), 1.2 (m,6H), 1.8 (m,2H), 3.1 (t,2H), 3.35 (s,3H), 3.45 (m,1H), 3.65 (m,2H), 4.6 (m,2H), 6.85 (d,2H), 6.9–7.1 (m,4H), 7.4 (d,1H), 9.1(s,1H), 11.8 (s,1H).

Example 7
Preparation of 3-propanoyl-4-(2-methylphenylamino)-8-(2-methylthioethoxy)quinoline.

A mixture of 3-propanoyl-4-chloro-8-(2-methylthioethoxy)quinoline (0.60 g, 1.9 mmol) and o-toluidine (0.25 g, 2.3 mmol) in acetonitrile was heated to 55° C. and stirred for 3.5 h. The solvent was evaporated and the residue was partitioned between methylene chloride and a 10% sodium carbonate solution. The organic layer was dried over sodium sulfate and evaporated. Chromatography ($SiO_2$; $CH_2Cl_2$:EtOAc 60:40) gave 0.45 g (61%) of the title compound.

($^1$H-NMR, 300 MHz,$CDCl_3$) 1.26 (t,3H), 2.21 (s,3H), 2.33 (s,3H), 3.06 (t,2H), 3.10 (q,2H), 4.33 (t,2H), 6.87 (d,1H), 6.96–7.12 (m,5H), 7.25 (d,1H), 9.26 (s,1H), 11.78 (s,1H).

Example 8
Preparation of 3-propanoyl-4-(2-methylphenylamino)-8-(2-methylsulfinylethoxy)quinoline.

3-Propanoyl-4-(2-methylphenylamino)-8-(2-methylthioethoxy)quinoline (0.10 g, 0.26 mmol) was dissolved in methylene chloride (5 ml). $NaHCO_3$ (45 mg) in $H_2O$ (5 ml) was added. The mixture was cooled to 4° C. A solution of 71% m-CPBA (0.062 g, 0.25 mmol) in methylene chloride (5 ml) was added dropwise. After stirring for 1 h at 2°–4° C., the organic layer was washed with a saturated sodium bicarbonate solution. The organic layer was dried over sodium sulfate and evaporated. Chromatography ($SiO_2$; $CH_2Cl_2$:EtOH 90:10) gave 50 mg (48%) of the desired product.

(1H-NMR, 300 MHz, $CDCl_3$) 1.26 (t,3H), 2.33 (s,3H), 2.78 (s,3H), 3.10–3.50 (m,4H), 4.61 (m,2H), 6.85 (d,1H), 6.92–7.11 (m,5H), 7.28 (d,1H), 9.18 (s,1H), 11.81 (s,1H).

Example 9
Preparation of 3-propanoyl-4-(2-methylphenylamino)-8-(2-methylsulfonylethoxy)quinoline.

3-Propanoyl-4-(2-methylphenylamino)-8-(2-methylthioethoxy)quinoline (0.12 g, 0.32 mmol) was dissolved in methylene chloride (5 ml). $NaHCO_3$ (110 mg) in $H_2O$ (10 ml) was added. The mixture was cooled to 4° C. A solution of 71% m-CPBA (0.17 g, 0.69 mmol) in methylene chloride (5 ml) was added dropwise. After stirring for 1 h at 2°–4° C., the organic layer was washed with a saturated sodium bicarbonate solution. The organic layer was dried over sodium sulfate and evaporated. Chromatography ($SiO_2$; $CH_2Cl_2$:EtOAc 50:50) gave 0.060 g (45%) of the title compound.

($^1$H-NMR, 300 MHz, $CDCl_3$) 1.26 (t,3H), 2.34 (d,3H), 3.15 (q,2H), 3.37 (s,3H), 3.61 (t,2H), 4.58 (t,2H), 6.86 (d,1H), 6.95–7.11 (m,5H), 7.26 (d,1H), 9.13 (s,1H), 11.81 (s,1H).

Example 10
Preparation of 3-propanoyl-4-(2-ethylphenylamino)-8-(2-methylthioethoxy)quinoline A mixture of 3-propanoyl-4-chloro-8-(2-methylthioethoxy)quinoline (0.093 g, 0.34 mmol) and 2-ethyl aniline (0.048 g, 0.39 mmol) in acetonitrile (1 ml) was heated to 65° C. and stirred 4.0 h. The solvent was evaporated and the residue was partitioned between methylene chloride and a saturated sodium bicarbonate solution. The organic layer was dried over sodium sulfate and evaporated. The residue was chromatographed ($SiO_2$; ethyl acetate) yielding 40 mg (30%) of the desired product.

($^1$H-NMR, 300 MHz, $CDCl_3$) 1.22–1.30 (m,6H), 2.22 (s,3H), 2.76 (q,2H) 3.06 (t,2H), 3.15 (q,2H), 4.34 (t,2H), 6.82 (d,1H), 6.91–7.06 (m,2H), 7.14 (m,1H), 7.28 (m,1H), 9.21 (s,1H), 11.83 (s,1H).

Examples 11 and 12
Preparation of 3-propanoyl-4-(2-ethylphenylamino)-8-(2-methylsulfinylethoxy)quinoline (Example 11) and 3-propanoyl-4-(2-ethylphenylamino)-8-(2-methylsulfonylethoxy)quinoline (Example 12)

3-Propanoyl-4-(2-ethylphenylamino)-8-(2-methylthioethoxy)quinoline (0.022 g, 0.056 mmol) was dissolved in methylene chloride (0.7 ml). $NaHCO_3$ (12 mg) in $H_2$ (0.7 ml) was added. The mixture was cooled to 4° C. A solution of 71% m-CPBA (0.017 g, 0.07 mmol) in methylene chloride (0.5 ml) was added dropwise. After stirring for 1 h at 2°–4° C., the organic layer was washed with a saturated sodium bicarbonate solution. The organic layer was dried over sodium sulfate and evaporated. Chromatography ($SiO_2$; $CH_2$:MeOH 90:10) gave 8 mg (35%) of the compound according to Example 11 and 10 mg (42%) of the compound according to Example 12. Example 11: ($^1$H-NMR, 300 MHz, $CDCl_3$): 1.25 (m,6H), 2.73–2.81 (m,5H), 3.15 (q, 2H), 3.22 (m, 1H), 3.41–3.49 (m,1H), 4.62 (m,2H), 6.84 (d,1H), 6.93–7.19 (m,5H), 7.31 (d,1H), 9.19 (s,1H), 11.88 (s,1H).

Example 12: ($^1$H-NMR, 300 MHz, $CDCl_3$): 1.29 (m,6H), 2.77 (q,2H), 3.16 (q,2H), 3.37 (s,3H), 3.61 (t,2H), 4.60 (t,2H), 6.85 (d,1H), 6.94–7.20 (m,5H), 7.31 (d,1H), 9.14 (s,1H), 11.90 (s,1H).

Example 13
Preparation of 3-butyryl-4-(4-fluoro-2-methylphenylamino)-8-(2-methylthioethoxy)quinoline A mixture of 3-butyryl-4-chloro-8-(2-methylthioethoxy) quinoline (2.75 g, 8.2 mmol) and 4-fluoro-2-methylaniline (1.34 g, 10.7 mmol) in acetonitrile (20 ml) was refluxed for 8 h. The solution was cooled and 1.52 g crystallized product was filtered off. The filtrate was evaporated and chromatographed ($SiO_2$; $CH_2Cl_2$:MeOH 95:5) yielding 0.4 g of the desired product. Total yield: 1.92 g (57%).

($^1$H-NMR, 300 MHz, $CDCl_3$) 1.05 (t, 3H), 1.85 (m, 2 H), 2.20 (s, 3 H), 2.30 (s, 3H), 3.05 (m, 4H), 4.35 (t, 2H), 6.75–6.90 (m, 2H), 7.00 (m, 4H), 9.20 (s, 1H), 11.80 (s,1H).

Examples 14 and 15
Preparation of 3-butyryl-4-(4-fluoro-2-methylphenylamino)-8-(2-methylsulfinylethoxy)quinoline (Example 14) and 3-butyryl-4-(4-fluoro-2-methylphenylamino)-8-(2-methylsulfonylethoxy)quinoline (Example 15)

3-butyryl-4-(4-fluoro-2-methylphenylamino)-8-(2-methylthioethoxy) quinoline (1.6 g, 3.88 mmol) was dissolved in methylene chloride (35 ml). 0.3M NaHCO$_3$-solution (36 ml) was added. The mixture was cooled to 4° C. A solution of 70% m-CPBA (1.22 g, 5.04 mmol) in methylene chloride (16 ml) was added dropwise. After stirring for 1 h at 2°–4° C., the organic layer was washed with 0.3M NaHCO$_3$-solution. The organic layer was dried over Na$_2$SO$_4$ and evaporated. Chromatography (SiO$_2$; CH$_2$Cl$_2$:MeOH 95:5) gave 1.55 g (93%) of the compound according to Example 14 and 0.31 g (18%) of the compound according to Example 15.

Example 14: ($^1$H-NMR, 300 MHz, CDCl$_3$) 0.95 (t, 3H), 1.75 (m, 2H), 2.20 (s, 3H), 2.70 (s, 3H), 3.00 (t, 2H), 3.10 (m, 1H), 3.30–3.40 (m, 1H), 4.50 (m, 2H), 6.70 (m, 1H), 6.75 (m, 1H), 6.85–6.95 (m, 3H), 7.00 (m, 1H), 9.10 (s, 1H), 11.85 (s,1H).

Example 15: ($^1$H-NMR, 300 MHz, CDCl$_3$): 1.05 (t, 3H), 1.80 (m, 2H), 2.30 (s, 3H), 3.10 (t, 2H), 3.40 (s, 3H), 3.60 (t, 2H), 4.60 (t, 2H), 6.75–6.80 (m, 1H), 6.85–6.90 (m, 1H), 6.95–7.05 (m, 4H), 9.15 (s, 1H), 11.85 (s,1H).

Example 16
Preparation of 3-propanoyl-4(2-isopropylphenylamino)-8-(2-methylthioethoxy)quinoline A mixture of 3-propanoyl-4-chloro-8-(2-methylthioethoxy)quinoline (305 mg, 1 mmol) and 2-isopropylaniline (1 ml) in 25 ml acetonitrile was refluxed overnight. The solvent was evaporated and the residue was partitioned between methylene chloride and a saturated sodium bicarbonate solution. The organic layer was dried over sodium sulfate and evaporated. The residue was chromatographed on a prep-TLC (methylene chloride:ethyl acetate 1:1) yielding 30 mg (8%) of the desired product.

($^1$H-NMR, 300 MHz, CDCl$_3$) 1.3 (m,9H), 2.25 (s,3H), 3.05 (t,2H), 3.15 (q,2H), 3.4 (m,1H), 4.3 (t,2H), 6.8 (d,1H), 7.0 (m,4H), 7.2 (t,1H), 7.4 (d,1H), 9.2 (s,1H).

Example 17
Preparation of 3-butyryl-4-(2-ethylphenylamino)-8-(2-methylthioethoxy) quinoline A mixture of 3-butyryl-4-chloro-8-(2-methylthioethoxy) quinoline (3.69 g, 9.84 mmol) and 2-ethylaniline (1.55 g, 12.8 mmol) in acetonitrile (20 ml) was refluxed for 6 h. The solution was evaporated. Chromatography (SiO$_2$; CH$_2$Cl$_2$:MeOH 97:3) gave 2.79 g (69%) of the desired product.

($^1$H-NMR, 300 MHz, CDCl$_3$) 1.00 (t, 3H), 1.25 (t, 3H), 1.80 (m, 2H), 2.20 (s, 3H), 2.80 (m, 2H), 3.10 (m, 4H), 4.35 (t, 2H), 6.85 (m, 1H), 6.90–7.10 (m, 4H), 7.15 (t, 1H), 7.30 (m, 1H), 9.20 (s, 1H).

Examples 18 and 19
Preparation of 3-butyryl-4-(2-ethylphenylamino)-8-(2-methylsulfinylethoxy)-quinoline (Example 18) and 3-butyryl-4-(2-ethylphenylamino)-8-(2-methylsulfonylethoxy)quinoline (Example 19).

3-butyryl-4-(2-ethylphenylamino)-8-(2-methylthioethoxy)quinoline (1.98 g, 4.85 mmol) was dissolved in methylene chloride (40 ml). 0.3M NaHCO$_3$ solution (45 ml) was added. The mixture was cooled to 4° C. A solution of 70% m-CPBA (1.54 g, 6.31 mmol) in methylene chloride (20 ml) was added dropwise. After stirring for 1 h at 2°–4° C., the organic layer was washed with 0.3M NaHCO$_3$ solution. The organic layer was dried over NaSO$_4$ and evaporated. Chromatography (SiO$_2$; CH$_2$Cl$_2$:MeOH 97:3) gave 0.62 g (30%) of Example 18 and 0.39 g (18%) of Example 19.

Example 18: (1H-NMR, 300 MHz, CDCl$_3$): 1.05 (t, 3H), 1.30 (t, 3H), 1.85 (m, 2H), 2.75 (m, 2H), 2.85 (s, 3H), 3.05 (t, 2H), 3.20–3.30 (m, 1H), 3.40–3.50 (m, 1H), 4.65 (m, 2H), 6.85 (m, 1H), 6.90–7.00 (m, 1H), 7.05–7.10 (m, 3H), 7.15 (t, 1H), 7.30 (m, 1H), 9.20 (s, 1H), 11.95 (s,1H).

Example 19: ($^1$H-NMR, 300 MHz, CDCl$_3$): 1.05 (t, 3H), 1.30 (t, 3H), 1.85 (m, 2H), 2.75 (m, 2H), 3.10 (t, 2H), 3.40 (s, 3H), 3.65 (m, 2H), 4.60 (m, 2H), 6.85 (d, 1H), 6.95–7.10 (m, 4H), 7.20 (t, 1H), 7.30 (m, 1H), 9.10 (s, 1H).

Example 20
Preparation of 3-propanoyl-4-(2-methylphenylamino)-8-(2-propylthioethoxy)quinoline.

3-Propanoyl-4-chloro-8-(2-propylthioethoxy)quinoline (2.5 g, 7.40 mmol) and o-toluidine (0.95 g, 8.86 mmol) was refluxed in acetonitrile (10 ml) for 2 h. The solvent was evaporated and the residue was partitioned between methylene chloride and 10% Na$_2$CO$_3$ solution. The organic layer was dried over Na$_2$SO$_4$ and evaporated. The crude product was purified by column chromatography (methylene chloride:ethyl acetate 80:20). 1.8 g (60%) of the title compound was obtained.

($^1$H-NMR, 300 MHz, CDCl$_3$) 1.00 (t, 3H), 1.28 (t, 3H) 1.66 (m, 2H), 2.35 (s, 3H) 2.62 (t, 2H), 3.09 (t, 2H), 3.14 (q, 2H), 4.32 (t, 2H), 6.80–7.25 (m, 7H), 9.22 (s, 1H), 11.76 (s, 1H).

Example 21
Preparation of 3-propanoyl-4-(2-methylphenylamino)-8-(2-propylsulfinylethoxy)quinoline.

3-Propanoyl-4-(2-methylphenylamino)-8-(2-propylthioethoxy)quinoline (0.5 g, 1.22 mmol) was dissolved in 10 ml methylene chloride. A solution of sodium bicarbonate (250 mg, 3.0 mmol) in 10 ml water was added. The mixture was cooled to 2°–4° C. A solution of 70% m-CPBA (295 mg, 1.20 mmol) in 10 ml methylene chloride was added dropwise during 10 min. The temperature was allowed to rise to room temperature and the mixture was stirred 30 min at this temperature. The organic layer was dried over Na$_2$SO$_4$ and evaporated. The residue was purified by column chromatography (methylene chloride:ethanol 90:10) to give 380 mg (73%) of the title compound.

($^1$H-NMR, 300 MHz, CDCl$_3$) 1.11 (t, 3H), 1.28 (t, 3H), 1.87 (m, 2H), 2.35 (s, 3H), 2.89 (m, 2H), 3.10–3.20 (m, 3H), 3.40 (m, 1H), 4.63 (q, 2H), 6.90–7.40 (m, 7H), 9.19 (s, 1H), 11.85 (s, 1H).

Example 22
Preparation of 3-propanoyl-4-(2-methylphenylamino)-8-(2-propylsulfonylethoxy)quinoline.

3-propanoyl-4-(2-methylphenylamino)-8-(2-propylthioethoxy)quinoline (500 mg, 1.22 mmol) was dissolved in 10 ml methylene chloride. A solution of sodium bicarbonate (500 mg, 5.95 mmol) in 10 ml water was added. The mixture was cooled to 2°–4° C. A solution of 70% m-CPBA (600 mg, 2.43 mmol) in 10 ml methylene chloride was added dropwise. The temperature was allowed to rise to room temperature and the stirring was continued for 30 min at this temperature. The methylene chloride layer was separated and washed with water. The organic layer was then dried over Na$_2$SO$_4$ and evaporated. The crude product was purified by column chromatography (methylene chloride: ethylacetate 50:50). 340 mg (63%) of the title compound was obtained.

(¹H-NMR, 300 MHz, CDCl₃) 1.13 (t, 3H), 1.27 (t, 3H), 1.96 (m, 2H), 2.35 (s, 3H), 3.16 (q, 2H), 3.47 (t, 2H), 3.58 (t, 2H), 4.58 (t, 2H), 6.85–7.25 (m, 7H), 9.12 (s, 1H), 11.81 (s, 1H).

Example 23
Preparation of 3-propanoyl-4-(2-methylphenylamino)-8-(3-propylthiopropoxy)quinoline.

3-Propanoyl-4-chloro-8-(3-propylthiopropoxy)quinoline (2.0 g, 5.7 mmol) and o-toluidine (0.7 g, 6.5 mmol) was refluxed in acetonitrile (10 ml) for 2 h. The solvent was evaporated and the residue was partitioned between methylene chloride and 10% Na₂CO₃ solution. The organic layer was dried over Na₂SO₄ and evaporated. The residue was purified by column chromatography (methylene chloride-:ethyl acetate 70:30). 1.3 g (54%) of the title compound was obtained.

(¹H-NMR, 300 MHz, CDCl₃) 0.94 (t, 3H), 1.26 (t, 3H), 1.57 (m, 2H), 2.25 (m, 2H), 2.34 (s, 3H), 2.49 (t, 2H), 2.75 (t, 2H), 3.15 (q, 2H), 4.27 (t, 2H) 6.83–7.23 (m, 7H), 9.22 (s, 1H), 11.73 (s, 1H).

Example 24
Preparation of 3-propanoyl-4-(2-methylphenylamino)-8-(3-propylsulfinylpropoxy)quinoline.

3-Propanoyl-4-(2-methylphenylamino)-8-(3-propylthiopropoxy)quinoline (200 mg, 0.47 mmol) was dissolved in 5 ml methylene chloride. A solution of sodium bicarbonate (80 mg, 0.95 mmol) in 5 ml water was added. The mixture was cooled to 2°–4° C. A solution of 70% m-CPBA (115mg, 0.47 mmol) in 5 ml methylene chloride was added dropwise during 10 min. The temperature was allowed to rise and the mixture was stirred for 30 min at room temperature. The methylene chloride layer was separated and washed with water. The organic layer was then dried over Na₂SO₄ and evaporated. The crude product was purified by column chromatography (methylene chloride: ethanol 95:5). 160 mg (77%) of the title compound was obtained.

(¹H-NMR, 300 MHz, CDCl₃) 1.06 (t, 3H), 1.27 (t, 3H), 1,79 (m, 2H), 2.33 (s, 3H), 2.49 (m, 2H), 2.60–2.80 (m, 3H), 2.93 (m, 1H), 3.17 (q, 2H), 4.34 (m, 2H), 6.85–7.30 (m, 7H), 9.26 (s, 1H), 12.01 (s, 1H).

Example 25
Preparation of 3-propanoyl-4-(2-methylphenylamino)-8-(3-propylsulfonylpropoxy)quinoline.

3-Propanoyl-4-(2-methylphenylamino)-8-(3-propylthiopropoxy)quinoline (200 mg, 0.47 mmol) was dissolved in 5 ml methylene chloride. A solution of sodium bicarbonate (160 mg, 1.90 mmol) in 5 ml water was added. The mixture was cooled to 2°–4° C. A solution of 70% m-CPBA (230 mg, 0.94 mmol) in 5 ml methylene chloride was added dropwise during 5 min. The temperature was allowed to rise and the mixture was stirred for 30 min at room temperature. The methylene chloride layer was separated and washed with water. The organic layer was then dried over Na₂SO₄ and evaporated. The crude product was purified by column chromatography (SiO₂; methylene chloride:ethyl acetate 50:50). 110 mg (51%) of the title compound was obtained.

(¹H-NMR, 300 MHz, CDCl₃): 1.06 (t, 3H), 1.28 (t, 3H), 1.88 (m, 2H), 2.35 (s, 3H), 2.50 (m, 2H), 2.97 (t, 2H), 3.16 (q, 2H), 3,32 (t, 2H), 4.35 (t, 2H), 6.85–7.30 (m, 7H), 9.19 (s, 1H), 11.78 (s, 1H).

Example 26
Preparation of 3-butyryl-4-(4-hydroxy-2-methylphenylamino)-8-(2-methylthioethoxy)quinoline A mixture of 3-butyryl-4-chloro-8-(2-methylthioethoxy)quinoline (2.48 g, 6.63 mmol) and 4-hydroxy-2-methylaniline (1.06 g, 8.62 mmol) in acetonitrile (20 ml) was refluxed for 8 h. The reaction mixture was evaporated and the residue was chromatographed (SiO₂; CH₂Cl₂:MeOH 95:5) yielding 1.22 g (45%) of the desired product.

(¹H-NMR, 300 MHz, CDCl₃) 1.05 (t, 3H), 1.80 (m, 2H), 2.20 (s, 6 H), 3.00–3.10 (m, 4H), 4.30 (m, 2H), 6.55 (m, 1H), 6.75–6.85 (m, 2 H), 6.95 (m, 2H), 7.00–7.10 (m, 1H), 9.15 (s, 1H).

Examples 27 and 28
Preparation of 3-butyryl-4-(4-hydroxy-2-methylphenylamino)-8-(2-methylsulfinylethoxy)quinoline (Example 27) and 3-butyryl-4-(4-hydroxy-2-methylphenylamino)-8-(2-methylsulfonylethoxy)quinoline (Example 28)

3-butyryl-4-(4-hydroxy-2-methylphenylamino)-8-(2-methylthioethoxy)-quinoline (1.06 g, 2.59 mmol) was dissolved in methylene chloride (25 ml). 0.3M NaHCO₃-solution (24 ml) was added. The mixture was cooled to 4° C. A solution of 70% m-CPBA (0.82 g, 3.37 mmol) in methylene chloride (15 ml) was added dropwise. After stirring for 1.5 h at 2°–4° C., the organic layer was washed with 0.3M NaHCO₃-solution. The organic layer was dried over Na₂SO₄ and evaporated. Chromatography on silica gel with EtOAc:CH₂Cl₂ 1:1 as eluent gave 0.4 g (35%) of Example 27 followed by CH₂Cl₂:MeOH 9:1 yielding 0.52 g (47%) of Example 28.

Example 27: (¹H-NMR, 300 MHz, CDCl₃) 1.05 (t, 3H), 1.80 (m, 2H), 2.20 (s, 3H), 2.75 (s, 3H), 3.05 (m, 2H), 3.10–3.20 (m, 1H), 3.40–3.50 (m, 1H), 4.55 (m, 2H), 6.55–6.60 (m, 1H), 6.75–6.80 (m, 2H), 6.90–6.95 (m, 1H), 7.00–7.10 (m, 2H), 9.15 (s, 1H).

Example 28: (¹H-NMR, 300 MHz, CDCl₃) 1.05 (t, 3H), 1.80 (m, 2H), 2.25 (s, 3H), 3.05 (t, 2H), 3.35 (s, 3H), 3.60 (m, 2H), 4.55 (m, 2H), 6.55–6.60 (m, 1H), 6.75 (m, 1H), 6.80–6.85 (m, 1H), 6.95–7.05 (m, 2H), 7.10 (m, 1H), 9.10 (s, 1H).

Example 29
Preparation of 3-butyryl-4-(2-chlorophenylamino)-8-(2-methylthioethoxy)quinoline A mixture of 3-butyryl-4-chloro-8-(2-methylthioethoxy)quinoline (0.8 g, 2.5 mmol) and 2-chloroaniline (0.47 g, 3.7 mmol) in toluene (12 ml) was heated to 90° C. and stirred 3.0 h. After cooling to room temperature, methylene chloride and water were added. The mixture was neutralized with a saturated solution of sodium bicarbonate. The organic layer was dried over sodium sulfate and evaporated. Trituration with isopropyl ether gave 0.84 g (81%) of the desired product.

(¹H-NMR, 300 MHz, CDCl₃): 1.05 (t, 3H), 1.80–1.90 (m, 2H), 2.25 (s, 3H), 3.10–3.15 (m, 4H), 4.35−4.40 (m, 2H), 6.80–6.90 (m, 1H), 7.05–7.15 (m, 5H), 7.45–7.50 (m, 1H), 9.30 (s, 1H), 11.55 (s,1H)

Example 30
Preparation of 3-butyryl-4-(2-chlorophenylamino)-8-(2-methylsulfinylethoxy)quinoline 3-butyryl-4-(2-chlorophenylamino)-8-(2-methylthioethoxy)quinoline (0.34g, 0.82 mmol) was dissolved in methylene chloride (4 ml). Water (2 ml) and sodium hypochlorite (5% in water) (1.37 ml) were added and the mixture was stirred for 2 h. Another portion of sodium hypochlorite (0.5 ml) was added and the stirring was continued for 2 h. The organic layer was dried over sodium sulfate and evaporated. The residue crystallized from a mixture of ethyl acetate and isopropyl ether and 0.25 g (71%) of the title compound was obtained.

($^1$H-NMR, 300 MHz, CDCl$_3$) 1.05 (t, 3H), 1.75–1.90 (m, 2H), 2.85 (s, 3H), 3.10 (t, 2H), 3.20–3.30 (m, 1H), 3.45–3.55 (m, 1H), 4.60–4.70 (m, 2H), 6.80–6.90 (m, 1H), 7.00–7.20 (m, 5H), 7.40–7.50 (m, 1H), 9.30 (s, 1H), 11.60 (s, 1H)

Example 31

Preparation of 3-butyryl-4-(2-chlorophenylamino)-8-(2-methylsulfonylethoxy)quinoline A mixture of 3-butyryl-4-(2-chlorophenylamino)-8-(2-methylthioethoxy)quinoline (0.4 g, 0.96 mmol) in methylene chloride (5 ml) and a saturated solution of sodium bicarbonate (5 ml) was cooled to 4° C. A solution of 70% m-CPBA (0.48 g, 1.97 mmol) in methylene chloride (5 ml) was added dropwise. After stirring for 1 h at 4° C., the organic layer was washed with a saturated solution of sodium bicarbonate and thereafter dried over sodium sulfate and evaporated. Trituration with isopropyl ether gave 0.28 g (65%) of the desired product.

($^1$H-NMR, 300 MHZ, CDCl$_3$) 1.05 (t, 3H), 1.75–1.90 (m, 2H), 3.10 (t, 2H), 3.40 (s, 3H), 3.60–3.70 (m, 2H), 4.60.4.70 (m, 2H), 6.85–6.90 (m, 1H), 7.00–7.20 (m, 5 H), 7.45–7.50 (m, 1H), 9.20 (s, 1H), 11.65 (s, 1H)

Example 32

Preparation of 3-butyryl-4-(2-methoxyphenylamino)-8-(2-methylthioethoxy)quinoline A mixture of 3-butyryl-4-chloro-8-(2-methylthioethoxy) quinoline (0.8 g, 2.5 mmol) and 2-methoxyaniline (0.45 g, 3.7 mmol) in toluene (12 ml) was heated to 90° C. and stirred 3.0 h. After cooling to room temperature, methylene chloride and water were added. The mixture was neutralized with a saturated solution of sodium bicarbonate. The organic layer was dried over sodium sulfate and evaporated. Trituration with isopropyl ether gave 0.80 g (77%) of the desired product.

($^1$H-NMR, 300 MHz, CDCl$_3$) 1.05 (t, 3H), 1.75–1.90 (m, 2H), 2.30 (s, 3H), 3.05–3.15 (m, 4H), 3.85 (s, 3H), 4.35–4.40 (m, 2H), 6.75–6.85 (m, 1H), 6.90–7.15 (m, 5 H), 7.25–7.30 (m, 1H), 9.25 (s, 1H), 11.55 (s, 1H)

Example 33

Preparation of 3-butyryl-4-(2-methoxyphenylamino)-8-(2-methylsulfinylethoxy)quinoline 3-butyryl-4-(2-methoxyphenylamino)-8-(2-methylthioethoxy)quinoline (0.35g, 0.85 mmol) was dissolved in methylene chloride (4 ml). Water (2 ml) and sodium hypochlorite (5% in water) (1.42 ml) were added and the mixture was stirred for 2 h. Another portion of sodium hypochlorite (0.5 ml) was added and the stirring was continued for 2 h. The organic layer was dried over sodium sulfate and evaporated. The residue crystallized from a mixture of ethyl acetate and isopropyl ether and 0.32 g (88%) of the title compound was obtained.

($^1$H-NMR, 300 MHz, CDCl$_3$): 1.05 (t, 3H), 1.75–1.90 (m, 2H), 2.80 (s, 3H),3.05–3.10 (m, 2H), 3.20–3.30 (m, 1H), 3.45–3.55 (m, 1H), 3.80 (s, 3H), 4.60.4.70 (m, 2H), 6.80–6.85 (m, 1H), 6.90–7.20 (m, 5H), 7.30–7.35 (m, 1H), 9.20 (s, 1H), 11.60 (s, 1H)

Example 34

Preparation of 3-butyryl-4-(2-methoxyphenylamino)-8-(2-methylsulfonylethoxy)quinoline A mixture of 3-butyryl-4-(2-methoxyphenylamino)-8-(2-methylthioethoxy)quinoline (0.35 g, 0.85 mmol) in methylene chloride (5 ml) and a saturated solution of sodium bicarbonate (5 ml) was cooled to 4° C. A solution of 70% m-CPBA (0.43 g, 1.74 mmol) in methylene chloride (5 ml) was added dropwise. After stirring for 1 h at 4° C., the organic layer was washed with a saturated solution of sodium bicarbonate and thereafter dried over sodium sulfate and evaporated. Trituration with isopropyl ether gave 0.28 g (65%) of the desired product.

($^1$H-NMR, 300 MHz, CDCl$_3$): 1.05 (t, 3H), 1.75–1.90 (m, 2H), 3.05–3.10 (m, 2H), 3.40 (s, 3H), 3.60–3.70 (m, 2H), 3.85 (s, 3H), 4.60–4.65 (m, 2H), 6.80–6.85 (m, 1H), 6.90–7.20 (m, 5H), 7.30–7.35 (m, 1H), 9.15 (s, 1H), 11.60 (s, 1H)

Example 35

Preparation of 3-butyryl-4-(2,4-dimethylphenylamino)-8-(2-methylthioethoxy)quinoline A mixture of 3-butyryl-4-chloro-8-(2-methylthioethoxy) quinoline (0.8 g, 2.5 mmol) and 2,4-dimethylaniline (0.45 g, 3.7 mmol) in toluene (12 ml) was heated to 90° C. and stirred 3.0 h. After cooling to room temperature, methylene chloride and water were added. The mixture was neutralized with a saturated solution of sodium bicarbonate. The organic layer was dried over sodium sulfate and evaporated. Trituration with isopropyl ether gave 0.77 g (75%) of the desired product.

($^1$H-NMR, 300 MHz, CDCl$_3$): 1.05 (t, 3H), 1.75–1.90 (m, 2H), 2.25 (s, 3H), 2.30 (s, 3H), 2.35 (s, 3H), 3.05–3.15 (m, 4H), 4.30–4.40 (m, 2H), 6.80–6.85 (m, 1H), 6.90–7.10 (m, 5H), 9.20 (s, 1H), 11.85 (s, 1H)

Example 36

Preparation of 3-butyryl-4-(2 4-dimethylphenylamino)-8-(2-methylsulfinylethoxy)quinoline 3-butyryl-4-(2,4-dimethylphenylamino)-8-(2-methylthioethoxy)quinoline (0.34g, 0.83 mmol) was dissolved in methylene chloride (4 ml). Water (2 ml) and sodium hypochlorite (5% in water) (1.39 ml) were added and the mixture was stirred for 2 h. Another portion of sodium hypochlorite (0.5 ml) was added and the stirring was continued for 2 h. The organic layer was dried over sodium sulfate and evaporated. Trituration with isopropyl ether gave 0.32 g (91%) of the title compound.

($^1$H-NMR, 300 MHz, CDCl$_3$) 1.05 (t, 3H), 1.75–1.90 (m, 2H), 2.30 (s, 3H), 2.35 (s, 3H), 2.80 (s, 3H), 3.05–3.15 (m, 2H), 3.20–3.30 (m, 1H), 3.40–3.55 (m, 1H), 4.60–4.65 (m, 2H), 6.80–6.85 (m, 1H), 6.90–7.15 (m, 5H), 9.15 (s, 1H), 11.85 (s, 1H)

Example 37

Preparation of 3-butyryl-4-(2,4-dimethylphenylamino)-8-(2-methylsulfonylethoxy)quinoline A mixture of 3-butyryl-4-(2,4-dimethylphenylamino)-8-(2-methylthioethoxy)quinoline (0.33 g, 0.81 mmol) in methylene chloride (5 ml) and a saturated solution of sodium bicarbonate (5 ml) was cooled to 4° C. A solution of 70% m-CPBA (0.40 g, 1.66 mmol) in methylene chloride (5 ml) was added dropwise. After stirring for 1 h at 4° C., the organic layer was washed with a saturated solution of sodium bicarbonate and thereafter dried over sodium sulfate and evaporated. After trituration with isopropyl ether a crystalline product was obtained. Chromatography (SiO$_2$; CH$_2$Cl$_2$:MEOH 90:10) gave 0.17 g (48%) of the desired compound.

($^1$H-NMR, 300 MHz, CDCl$_3$) 1.05 (t, 3H), 1.75–1.90 (m, 2H), 2.30 (s, 3H), 2.35 (s, 3H), 3.05–3.15 (m, 2H), 3.40 (s, 3H), 3.60–3.65 (m, 2H), 4.60–4.65 (m, 2H), 6.80–6.85 (m, 1H), 6.90–7.15 (m, 5H), 9.10 (s, 1H), 11.90 (s,1H)

Example 38

Preparation of 3-butyryl-4-(2,6-dimethylphenylamino)-8-(2-methylthioethoxy)quinoline A mixture of 3-butyryl-4-chloro-8-(2-methylthioethoxy) quinoline (0.8 g, 2.5 mmol) and 2,6-dimethylaniline (0.45 g, 3.7 mmol) in toluene (12 ml) was heated to 90° C. and stirred 3.0 h. After cooling to room temperature, methylene chloride and water were added. The mixture was neutralized with a saturated solution of sodium bicarbonate. The organic layer was dried over sodium sulfate and evaporated. Chromatography (SiO$_2$; EtOAc) gave 0.7 g (68%) of the title compound.

($^1$H-NMR, 300 MHz, CDCl$_3$) 1.05 (t, 3H), 1.75–1.90 (m, 2H), 2.10 (s, 6H), 2.25 (s, 3H), 3.05–3.15 (m, 4H), 4.304.35 (m, 2H), 6.85–7.20 (m, 6H), 9.20 (s, 1H), 12.25 (s, 1H)

Example 39
Preparation of 3-butyryl-4-(2,6-dimethylphenylamino)-8-(2-methylsulfinylethoxy)quinoline 3-butyryl-4-(2,6-dimethylphenylamino)-8-(2-methylthioethoxy)quinoline (0.33 g, 0.81 mmol) was dissolved in methylene chloride (4 ml). Water (2 ml) and sodium hypochlorite (5% in water) (1.7 ml) were added and the mixture was stirred for 3 h. The organic layer was dried over sodium sulfate and evaporated. Trituration with isopropyl ether gave 0.20 g (58%) of the title compound.

($^1$H-NMR, 300 MHz, CDCl$_3$) 1.05 (t, 3H), 1.80–1.90 (m, 2H), 2.10 (s, 3H), 2.15 (s, 3H), 2.80 (s, 3H), 3.10–3.15 (m, 2H), 3.20–3.30 (m, 1H), 3.40–3.55 (m, 1H), 4.55–4.65 (m, 2H), 6.85–6.95 (m, 2H), 7.05–7.25 (m, 4H), 9.20 (s, 1H), 12.25 (s, 1H)

Example 40
Preparation of 3-butyryl-4-(2,6-dimethylphenylamino)-8-(2-methylsulfonylethoxy)quinoline A mixture of 3-butyryl-4-(2,6-dimethylphenylamino)-8-(2-methylthioethoxy)quinoline (0.36 g, 0.88 mmol) in methylene chloride (5 ml) and a saturated solution of sodium bicarbonate (5 ml) was cooled to 4° C. A solution of 70% m-CPBA (0.42 g, 1.76 mmol) in methylene chloride (5 ml) was added dropwise. After stirring for 1 h at 4° C., the organic layer was washed with a saturated sodium bicarbonate solution and thereafter dried over sodium sulfate and evaporated. After trituration with isopropyl ether a crystalline product was obtained. Chromatography (SiO$_2$; CH$_2$Cl$_2$:MEOH 90:10) and finally crystallization from ethyl acetate gave 0.070 g (18%) of the desired product.

($^1$H-NMR, 300 MHz, CDCl$_3$) 1.05 (t, 3H), 1.80–1.95 (m, 2H), 2.10 (s, 6H), 3.05–3.15 (m, 2H), 3.40 (s, 3H), 3.60–3.65 (m, 2H), 4.554.60 (m, 2H), 6.85–6.95 (m, 2H), 7.00–7.25 (m, 4H), 9.10 (s, 1H), 12.30 (s,1H)

Example 41
Preparation of 3-butyryl-4-(2-methyl 6-chlorophenylamino)-8-(2-methylthioethoxy)quinoline A mixture of 3-butyryl-4-chloro-8-(2-methylthioethoxy) quinoline (0.8 g, 2.5 mmol) and 2-methyl, 6-chloroaniline (0.52 g, 3.7 mmol) in toluene (12 ml) was heated to 90° C. and stirred 3.0 h. After cooling to room temperature, methylene chloride and water were added. The mixture was neutralized with a saturated solution of sodium bicarbonate. The organic layer was dried over sodium sulfate and evaporated. Chromatography (SiO$_2$; EtOAc) gave 0.77 g (72%) of the title compound.

($^1$H-NMR, 300 MHz, CDCl$_3$) 1.05 (t, 3H), 1.80–1.90 (m, 2H), 2.15 (s, 3H), 2.25 (s, 3H), 3.05–3.15 (m, 4H), 4.30–4.40 (m, 2H), 6.85–6.90 (1H), 6.90–7.05 (m, 2H), 7.15–7.35 (m, 3H), 9.20 (s, 1H), 12.15 (s, 1H)

Example 42
Preparation of 3-butyryl-4-(2-methyl,6-chlorophenylamino) -8-(2-methylsulfinylethoxy)quinoline 3-butyryl-4-(2-methyl,6-chlorophenylamino)-8-(2-methylthioethoxy) quinoline (0.35 g, 0.82 mmol) was dissolved in methylene chloride (4 ml). Water (2 ml) and sodium hypochlorite (5% in water) (1.7 ml) were added and the mixture was stirred for 3 h. The organic layer was dried over sodium sulfate and evaporated. The residue crystallized from ethyl acetate and 0.10 g (27%) of the title compound was obtained.

($^1$H-NMR, 300 MHz, CDCl$_3$) 1.05 (t, 3H), 1.80–1.90 (m, 2H), 2.15 (m, 3H), 2.85 (m, 3H), 3.10–3.15 (m, 2H), 3.20–3.30 (m, 1H), 3.40–3.55 (m, 1H), 4.55–4.70 (m, 2H), 6.85–7.00 (m, 2H), 7.05–7.10 (m, 1H), 7.15–7.35 (m, 3H), 9.20 (s, 1H), 12.20 (s, 1H)

Example 43
Preparation of 3-butyryl-4-(2-methyl,6-chlorophenylamino) -8-(2-methylsulfonylethoxy)quinoline A mixture of 3-butyryl-4-(2-methyl,6-chlorophenylamino)-8-(2-methylthioethoxy)quinoline (0.34 g, 0.79 mmol) in methylene chloride (5 ml) and a saturated solution of sodium bicarbonate (5 ml) was cooled to 4° C. A solution of 70% m-CPBA (0.38 g, 1.58 mmol) in methylene chloride (5 ml) was added dropwise. After stirring for 1 h at 4° C., the organic layer was washed with a saturated sodium bicarbonate solution and thereafter dried over sodium sulfate and evaporated. Crystallization from ethyl acetate gave 0.11 g (30%) of the desired product.

($^1$H-NMR, 300 MHz, CDCl$_3$) 1.05 (t, 3H), 1.80–1.95 (m, 2H), 2.15 (s, 3H), 3.05–3.15 (m, 2H), 3.40 (s, 3H), 3.60–3.70 (m, 2H), 4.554.65 (m, 2H), 6.90–7.05 (m, 3H), 7.15–7.25 (m, 2H), 7.30–7.35 (m, 1H), 9.15 (s, 1H), 12.20 (s, 1H)

Example 44
Preparation of 3-propanoyl-4-(2-methylphenylamino)-8-(3-methylthiopropoxy)quinoline.

3-Propanoyl-4-chloro-8-(3-methylthiopropoxy)quinoline (1.2 g, 3.71 mmol) and o-toluidine (0.795 g, 7.42 mmol) was refluxed in acetonitrile (18 ml) for 100 min. The solvent was evaporated and the residue was purified by column chromatography (methylene chloride:methanol 100:3). 1.45 g (99%) of the title compound was obtained.

($^1$H-NMR, 300 MHz, CDCl$_3$) 1.3 (t, 3H), 2.15 (s, 3H), 2.2–2.3 (m, 2H), 2.33 (s, 3H), 2.75 (t, 2H), 3.15 (q, 2H), 4.28 (t, 2H), 6.83–6.92 (m, 1H), 6.95–7.18 (m, 5H), 7.25–7.33 (m, 1H),9.25 (s, 1H), 11.75 (s, 1H).

Examples 45 and 46
Preparation of 3-propanoyl-4-(2-methylphenylamino)-8-(3-methylsulfinylpropoxy)quinoline (Example 45) and 3-propanoyl-4-(2-methylphenylamino)-8-(3-methylsulfonylpropoxy)quinoline (Example 46).

3-Propanoyl-4-(2-methylphenylamino)-8-(3-methylthiopropoxy) quinoline (1.03 g, 2.611 mmol) was dissolved in methylene chloride (30 ml). 0.3M NaHCO$_3$ solution (26 ml, 7.83 mmol) was added. The mixture was cooled to 4° C. A solution of 70.5% m-CPBA (0.895 g, 3.66 mmol) in methylene chloride (27 ml) was added dropwise over a 45 min period. After stirring for 30 min at 4° C., the organic layer was separated and washed with 0.3M NaHCO$_3$ solution. The organic layer was dried over Na$_2$SO$_4$ and evaporated. Column chromatography (SiO$_2$; CH$_2$Cl$_2$:MeOH 100:3 and 100:6) gave 0.48 g (45%) of the compound according to Example 45 and 0.50 g (45%) of the compound according to Example 46.

Example 45: ($^1$H-NMR, 300 MHz, CDCl$_3$) 1.3 (t, 3H), 2.38 (s, 3H), 2.44–2.55 (m, 2H), 2.65 (s, 3H), 2.9–3.02 (m, 1H), 3.08–3.23 (m, 3H), 4.28–4.4 (m, 2H), 6.85–6.92 (m, 1H), 6.95–7.18 (m, 5H), 7.25–7.34 (m, 1H), 9.25 (s, 1H), 11.8 (s, 1H)

Example 46: ($^1$H-NMR, 300 MHz, CDCl$_3$) 1.28 (t,3H), 2.35 (s, 3H), 2.45–2.58 (m, 2H), 2.95 (s, 3H), 3.18 (q, 2H), 3.4 (t, 2H), 4.35 (t, 2H), 6.85–6.92 (m, 1H), 6.95–7.15 (m, 5H), 7.22–7.33 (m, 1H), 9.23 (s, 1H), 11.83 (s, 1H)

Example 47
Preparation of 3-butyryl-4-(2-chlorophenylamino)-8-(3-methylthiopropoxy)quinoline.

A mixture of 3-butyryl-4-chloro-8-(3-methylthiopropoxy) quinoline (0.95 g, 2.8 mmol) and 2-chloroaniline (1.51 g, 11.8 mmol) in toluene was heated to 55° C. and stirred overnight. The solvent was evaporated and the residue was partioned between methylene chloride and a saturated sodium bicarbonate solution. The organic layer was dried over Na$_2$SO$_4$ and evaporated. The residue was chromatographed (SiO$_2$; CH$_2$Cl$_2$:MeOH 95:5) yielding 0.95 g (74%) of the desired product.

($^1$H-NMR, 500 MHz, CDCl$_3$) 0.95–1.05 (t 3H), 1.75–1.85 (m, 2H), 2.10 (s, 3H), 2.20–2.30 (m, 2H), 2.70–2.80 (m, 2H), 3.0–3.10 (m, 2H), 4.20–4.30 (m, 2H), 6.80 (d, 1H), 6.95–7.10 (m, 5H), 7.40 (d, 1H), 9.20 (s, 1H), 11.6 (s, 1H).

Example 48
Preparation of 3-butyl-4-(2-chlorophenylamino)-8(3-methylsulfinylpropoxy)quinoline.

3-butyryl-4-(2-chlorophenylamino)-8-(3-methylthiopropoxy)quinoline (0.31 g, 0.72 mmol) was dissolved in methylene chloride (10 ml), 5 ml water was added and then a solution of 1.5 ml (1.09 mmol) of 5% NaOCl in 10 ml methylene chloride was added. The mixture was stirred for 4 h at room temperature. The organic phase was separated and evaporated. Chromatography with methylene chloride:methanol 95:5 as the eluent gave 0.104g (32%) of the title compound.

($^1$H-NMR, 500 MHz, CDCl$_3$) 1.05 (t, 3H), 1.80–1.90 (m, 3H), 2.45–2.55 (m, 2H), 2.65 (s, 3H), 2.90–3.0 (m, 1H), 3.05–3.15 (m, 2H), 3.15–3.20 (m, 1H), 4.30–4.40 (m, 2H), 6.85 (d, 1H), 7.0–7.15 (m, 5H), 7.45 (d, 1H), 9.25 (s, 1H), 11.60 (s, 1H)

Example 49
Preparation of 3-butyryl-4-(2-chlorophenylamino)-8(3-methylsulfonylpropoxy)quinoline.

A mixture of 3-butyryl-4(2-chlorophenylamino)-8-(3-methylthiopropoxy)quinoline (0.31 g, 0.72 mmol) in 5 ml methylene chloride and NaHCO$_3$ (0.27 g, 3.2 mmol) in 5 ml H$_2$O was cooled to 4° C. A solution of 70% m-CPBA (0.4 g, 1.63 mmol) in 10 ml methylene chloride was added dropwise. After stirring for 1 h at 4° C., the organic layer was washed with a saturated sodium bicarbonate solution. The organic layer was dried over Na$_2$SO$_4$ and evaporated. Chromatography (SiO$_2$; CH$_2$Cl$_2$:MeOH 95:5) gave 69 mg (21%) of the desired product.

($^1$H-NMR, 500 MHz, CDCl$_3$) 1.05 (t, 3H), 1.80–1.90 (m, 2H), 2.50–2.55 (m, 2H), 3.00 (s, 3H), 3.05–3.10 (m, 2H), 3.40–3.45 (m, 2H), 4.35–4.40 (m, 2H), 6.80–6.85 (m, 1H), 7.00–7.20 (m, 5H), 7.45–7.50 (m, 1H), 9.25 (s, 1H), 11.60 (s, 1H)

Example 50
Preparation of 3-butyryl-4-(2-methylphenylamino)-8-(3-methylthiopropoxy)quinoline.

A mixture of 3-butyryl-4-chloro-8-(3-methylthiopropoxy) quinoline (0.95 g, 2.97 mmol) and 2-methylaniline (1.27 g, 11.8 mmol) in toluene was heated to 55° C. and stirred overnight. The solvent was evaporated and the residue was partioned between methylene chloride and a saturated sodium bicarbonate solution. The organic layer was dried over Na$_2$SO$_4$ and evaporated. The residue was chromatographed (SiO$_2$ ; CH$_2$Cl$_2$:MeOH 95:5) yielding 0.98 g (80.9%) of the desired product.

($^1$H-NMR, 500 MHz, CDCl$_3$) 1.05 (t, 3H), 1.75–1.80 (m, 2H), 2.10 (s, 3H), 2.25–2.30 (m, 2H), 2.35 (s, 3H), 2.75–2.80 (m, 2H), 3.05–3.10 (m, 2H), 4.25–4.30 (m, 2H), 7.85–7.90 (d, 1H), 6.95–7.15 (m, 5H), 7.25 (d, 1H), 9.20 (s, 1H), 11.75 (s, 1H)

Example 51
Preparation of 3-butyryl-4-(2-methylphenylamino)-8(3-methylsulfinylpropoxy)quinoline.

3-butyryl-4-(2-methylphenylamino)-8-(3-methylthiopropoxy)quinoline (0.33 g, 0.8 mmol) was dissolved in methylene chloride (15 ml), 5 ml water was added and then a solution of 1.5 ml (1.09 mmol) of 5% NaOCl in 10 ml methylene chloride was added. The mixture was stirred for 4 h at room temperature. The organic phase was separated and evaporated. Chromatography with methylene chloride: methanol 95:5 as the eluent gave 0.18 g (53%) of the title compound.

($^1$H-NMR, 500 MHz, CDCl$_3$) 1.05 (t, 3H), 1.75–1.85 (m, 2H), 2.30 (s, 3H), 2.40–2.50 (m, 2H), 2.60 (s, 3H), 2.90–3.15 (m, 4H), 4.25–4.40 (m, 2H), 6.85–6.90 (m, 1H), 6.95–7.15 (m, 5H), 7.25–7.30 (m, 1H), 9.20 (s, 1H), 11.90 (s, 1H)

Example 52
Preparation of 3-butyryl-4-(2-methylphenylamino)-8(3-methylsulfonylpropoxy)quinoline.

A mixture of 3-butyryl-4(2-methylphenylamino)-8-(3-methylthiopropoxy)quinoline (0.33 g, 0.81 mmol) in 5 ml methylene chloride and NaHCO$_3$ (0.27 g, 3.2 mmol) in 5 ml H$_2$O was cooled to 4° C.

A solution of 70% m-CPBA (0.4 g, 1.63 mmol) in 10 ml methylene chloride was added dropwise. After stirring for 1 h at 4° C., the organic layer was washed with a saturated sodium bicarbonate solution. The organic layer was dried over Na$_2$SO$_4$ and evaporated. Chromatography (SiO$_2$; CH$_2$Cl$_2$:MeOH 95:5) gave 99 mg (28%) of the desired product.

($^1$H-NMR, 500 MHz, CDCl$_3$): 1.05 (t, 3H), 1.80–1.90 (m, 2H), 2.35 (s, 3H), 2.50–2.55 (m, 2H), 3.00 (s, 3H), 3.10–3.15 (m, 2H), 3.35–3.45 (m, 2H), 4.35–4.40 (m, 2H), 6.85–6.90 (m, 1H), 6.95–7.15 (m, 5H), 7.25–7.30 (m, 1H), 9.20 (s, 1H), 11.85 (s, 1H)

Example 53
Preparation of 3-butyryl-4-(2-methoxyphenylamino)-8-(3-methylthiopropoxy)quinoline.

A mixture of 3-butyryl-4-chloro-8-(3-methylthiopropoxy) quinoline (0.95 g, 2.97 mmol) and 2-methoxyaniline (1.46 g, 11.8 mmol) in toluene was heated to 55° C. and stirred overnight. The solvent was evaporated and the residue was partitioned between methylene chloride and a saturated sodium bicarbonate solution. The organic layer was dried over Na$_2$SO$_4$ and evaporated. The residue was chromatographed (SiO$_2$; CH$_2$Cl$_2$:MeOH 95:5) yielding 0.90 g (71%) of the desired product.

($^1$H-NMR, 300 MHz, CDCl$_3$): 1.05 (t, 3H), 1.75–1.90 (m, 2H), 2.10 (s, 3H), 2.25–2.35 (m, 2H), 2.75–2.80 (m, 2H), 3.05–3.10 (m, 2H), 3.80 (s, 3H), 4.25–4.35 (m, 2H), 6.75–6.85 (m, 1H), 6.90–7.20 (m, 5H), 7.25–7.30 (m, 1H), 9.20 (s, 1H), 11.65 (s, 1H)

Example 54
Preparation of 3-butyryl-4-(2-methoxyphenylamino)-8(3-methylsulfinylpropoxy)quinoline.

3-butyryl-4-(2-methoxyphenylamino)-8-(3-methylthiopropoxy)quinoline (0.30 g, 0.70 mmol) was dissolved in methylene chloride (10 ml), 5 ml water was added and then a solution of 1.5 ml (1.09 mmol) of 5% NaOCl in 10 ml methylene chloride was added. The mixture was stirred for 4 h at room temperature. The organic phase was separated and evaporated. Chromatography with methylene chloride methanol 95:5 as the eluent gave 14 mg (4.6%) of the title compound.

($^1$H-NMR, 500 MHz, CDCl$_3$) 1.0 (t, 3H), 1.75–1.85 (m, 2H), 2.45–2.55 (m, 2H), 2.63 (s, 3H), 2.95 (m, 1H), 3.05–3.10 (m, 2H), 3.15 (m, 1H), 3.8 (s, 3H), 4.30 (m, 1H), 4.40 (m, 1H), 6.80–7.20 (m, 6H), 7.30 (m, 1H), 9.20 (s,1H), 11.6 (s, 1H)

Example 55
Preparation of 3-butyryl-4-(2-methoxyphenylamino)-8(3-methylsulfonylpropoxy)quinoline.

A mixture of 3-butyryl-4(2-methoxyphenylamino)-8-(3-methylthiopropoxy)quinoline (0.30 g, 0.71 mmol) in 5 ml methylene chloride and NaHCO$_3$ (0.27 g, 3.2 mmol) in 5 ml H$_2$O was cooled to 4° C. A solution of 70% m-CPBA (0.4 g, 1.63 mmol) in 10 ml methylene chloride was added dropwise. After stirring for 1 h at 4° C., the organic layer was washed with a saturated sodium bicarbonate solution. The organic layer was dried over Na$_2$SO$_4$ and evaporated. Chromatography (SiO$_2$; CH$_2$Cl$_2$:MeOH 95:5) gave 41 mg (13%) of the desired product.

($^1$H-NMR, 500 MHz, CDCl$_3$) 1.05 (t, 3H), 1.80–1.90 (m, 2H), 2.50–2.55 (m, 2H), 3.00 (s, 3H), 3.05–3.10 (m, 2H), 3.40–3.45 (m, 2H), 3.80 (s, 3H), 4.35–4.40 (m, 2H), 6.80–7.15 (m, 6H), 7.30–7.35 (m, 1H), 9.20 (s, 1H), 11.60 (s, 1H)

Example 56
Resolution of 3-butyryl-4-(2-methylphenylamino)-8-(2-methylsulfinylethoxy)quinoline A mixture of 3-butyryl-4-(2-methylphenylamino)-8-(2-methylsulfinylethoxy)quinoline (9.3 g, 0.023 mmol) and D-(−)-tartaric acid (3.45 g, 0.023 mmol) in methanol (180 ml) was heated to reflux. The solution was allowed to cool to room temperature and stirred for 60 h. The precipitate was filtered off and washed with a total amount of 20 ml methanol giving 6.1 g of the tartaric salt (the filtrate was used in Example 57). Recrystallization from methanol was repeated 3 times yielding 3.05 g, 1.30 g and finally 1.05 g of the tartaric salt of Example 57. The salt was neutralized with a saturated sodium bicarbonate in methylene chloride and water. The organic layer was dried over sodium sulfate and the solvent was evaporated. Trituration with isopropyl ether gave 0.7 g of the pure enantiomer.

Example 57
Resolution of 3-butyryl-4-(2-methylphenylamino)-8-(2-methylsulfinylethoxy)quinoline The filtrate from the first crystallization in Example 56 was evaporated. The salt was neutralized with a saturated sodium bicarbonate solution in methylene chloride and water. The organic layer was dried over sodium sulfate and the solvent was evaporated. The solid residue (4.6 g, 0.011 mole) and L-(+)-tartaric acid (1.68 g, 0.011 mole) were dissolved in warm methanol (110 ml). The solution was allowed to cool to room temperature and stirred for 72 h. The precipitate was filtered off and washed with a total amount of 11 ml methanol giving 1.5 g of the tartaric salt. Recrystallization from methanol gave 1.05 g of the tartaric salt of Example 57. The salt was neutralized with a saturated sodium bicarbonate solution in methylene chloride and water. The organic layer was dried over sodium sulfate and the solvent was evaporated. Trituration with isopropyl ether gave 0.7 g of the pure enantiomer.

The enantiomers were separated on a 250×4.6 mm i.d. Chiralpak AD column (Daciel, Japan) using the following parameters: n-hexane: 2-propanol: acetonitrile: diethyl amine (82:18:2:0.1); temperature: 35° C.; flow rate: 0.8 ml/min.

Enantiomer according to Example 56: retention time 14.5 min

Enantiomer according to Example 57: retention time 18.4 min

TABLE 1

Summary of the exemplified compounds of the invention.

| Example | R$^1$ | R$^2$ | R$^3$ | R$^4$ | m | n |
|---|---|---|---|---|---|---|
| 1 | CH$_2$CH$_2$CH$_3$ | CH$_3$ | CH$_3$ | H | 2 | 0 |
| 2 | CH$_2$CH$_2$CH$_3$ | CH$_3$ | CH$_3$ | H | 2 | 1 |
| 3 | CH$_2$CH$_2$CH$_3$ | CH$_3$ | CH$_3$ | H | 2 | 2 |
| 4 | CH$_2$CH$_2$CH$_3$ | CH(CH$_3$)$_2$ | CH$_3$ | H | 2 | 0 |
| 5 | CH$_2$CH$_2$CH$_3$ | CH(CH$_3$)$_2$ | CH$_3$ | H | 2 | 1 |
| 6 | CH$_2$CH$_2$CH$_3$ | CH(CH$_3$)$_2$ | CH$_3$ | H | 2 | 2 |
| 7 | CH$_2$CH$_3$ | CH$_3$ | CH$_3$ | H | 2 | 0 |
| 8 | CH$_2$CH$_3$ | CH$_3$ | CH$_3$ | H | 2 | 1 |
| 9 | CH$_2$CH$_3$ | CH$_3$ | CH$_3$ | H | 2 | 2 |
| 10 | CH$_2$CH$_3$ | CH$_2$CH$_3$ | CH$_3$ | H | 2 | 0 |
| 11 | CH$_2$CH$_3$ | CH$_2$CH$_3$ | CH$_3$ | H | 2 | 1 |
| 12 | CH$_2$CH$_3$ | CH$_2$CH$_3$ | CH$_3$ | H | 2 | 2 |
| 13 | CH$_2$CH$_2$CH$_3$ | CH$_3$ | CH$_3$ | 4-F | 2 | 0 |
| 14 | CH$_2$CH$_2$CH$_3$ | CH$_3$ | CH$_3$ | 4-F | 2 | 1 |
| 15 | CH$_2$CH$_2$CH$_3$ | CH$_3$ | CH$_3$ | 4-F | 2 | 2 |
| 16 | CH$_2$CH$_3$ | CH(CH$_3$)$_2$ | CH$_3$ | H | 2 | 0 |
| 17 | CH$_2$CH$_2$CH$_3$ | CH$_2$CH$_3$ | CH$_3$ | H | 2 | 0 |
| 18 | CH$_2$CH$_2$CH$_3$ | CH$_2$CH$_3$ | CH$_3$ | H | 2 | 1 |
| 19 | CH$_2$CH$_2$CH$_3$ | CH$_2$CH$_3$ | CH$_3$ | H | 2 | 2 |
| 20 | CH$_2$CH$_3$ | CH$_3$ | CH$_2$CH$_2$CH$_3$ | H | 2 | 0 |
| 21 | CH$_2$CH$_3$ | CH$_3$ | CH$_2$CH$_2$CH$_3$ | H | 2 | 1 |
| 22 | CH$_2$CH$_3$ | CH$_3$ | CH$_2$CH$_2$CH$_3$ | H | 2 | 2 |
| 23 | CH$_2$CH$_3$ | CH$_3$ | CH$_2$CH$_2$CH$_3$ | H | 3 | 0 |
| 24 | CH$_2$CH$_3$ | CH$_3$ | CH$_2$CH$_2$CH$_3$ | H | 3 | 1 |
| 25 | CH$_2$CH$_3$ | CH$_3$ | CH$_2$CH$_2$CH$_3$ | H | 3 | 2 |
| 26 | CH$_2$CH$_2$CH$_3$ | CH$_3$ | CH$_3$ | 4-OH | 2 | 0 |
| 27 | CH$_2$CH$_2$CH$_3$ | CH$_3$ | CH$_3$ | 4-OH | 2 | 1 |
| 28 | CH$_2$CH$_2$CH$_3$ | CH$_3$ | CH$_3$ | 4-OH | 2 | 2 |
| 29 | CH$_2$CH$_2$CH$_3$ | Cl | CH$_3$ | H | 2 | 0 |
| 30 | CH$_2$CH$_2$CH$_3$ | Cl | CH$_3$ | H | 2 | 1 |
| 31 | CH$_2$CH$_2$CH$_3$ | Cl | CH$_3$ | H | 2 | 2 |
| 32 | CH$_2$CH$_2$CH$_3$ | OCH$_3$ | CH$_3$ | H | 2 | 0 |
| 33 | CH$_2$CH$_2$CH$_3$ | OCH$_3$ | CH$_3$ | H | 2 | 1 |
| 34 | CH$_2$CH$_2$CH$_3$ | OCH$_3$ | CH$_3$ | H | 2 | 2 |
| 35 | CH$_2$CH$_2$CH$_3$ | CH$_3$ | CH$_3$ | 4-CH$_3$ | 2 | 0 |
| 36 | CH$_2$CH$_2$CH$_3$ | CH$_3$ | CH$_3$ | 4-CH$_3$ | 2 | 1 |
| 37 | CH$_2$CH$_2$CH$_3$ | CH$_3$ | CH$_3$ | 4-CH$_3$ | 2 | 2 |
| 38 | CH$_2$CH$_2$CH$_3$ | CH$_3$ | CH$_3$ | 6-CH$_3$ | 2 | 0 |
| 39 | CH$_2$CH$_2$CH$_3$ | CH$_3$ | CH$_3$ | 6-CH$_3$ | 2 | 1 |
| 40 | CH$_2$CH$_2$CH$_3$ | CH$_3$ | CH$_3$ | 6-CH$_3$ | 2 | 2 |
| 41 | CH$_2$CH$_2$CH$_3$ | CH$_3$ | CH$_3$ | 6-Cl | 2 | 0 |
| 42 | CH$_2$CH$_2$CH$_3$ | CH$_3$ | CH$_3$ | 6-Cl | 2 | 1 |
| 43 | CH$_2$CH$_2$CH$_3$ | CH$_3$ | CH$_3$ | 6-Cl | 2 | 2 |
| 44 | CH$_2$CH$_3$ | CH$_3$ | CH$_3$ | H | 3 | 0 |
| 45 | CH$_2$CH$_3$ | CH$_3$ | CH$_3$ | H | 3 | 1 |
| 46 | CH$_2$CH$_3$ | CH$_3$ | CH$_3$ | H | 3 | 2 |
| 47 | CH$_2$CH$_2$CH$_3$ | Cl | CH$_3$ | H | 3 | 0 |
| 48 | CH$_2$CH$_2$CH$_3$ | Cl | CH$_3$ | H | 3 | 1 |
| 49 | CH$_2$CH$_2$CH$_3$ | Cl | CH$_3$ | H | 3 | 2 |
| 50 | CH$_2$CH$_2$CH$_3$ | CH$_3$ | CH$_3$ | H | 3 | 0 |
| 51 | CH$_2$CH$_2$CH$_3$ | CH$_3$ | CH$_3$ | H | 3 | 1 |
| 52 | CH$_2$CH$_2$CH$_3$ | CH$_3$ | CH$_3$ | H | 3 | 2 |
| 53 | CH$_2$CH$_2$CH$_3$ | OCH$_3$ | CH$_3$ | H | 3 | 0 |
| 54 | CH$_2$CH$_2$CH$_3$ | OCH$_3$ | CH$_3$ | H | 3 | 1 |
| 55 | CH$_2$CH$_2$CH$_3$ | OCH$_3$ | CH$_3$ | H | 3 | 2 |

2. PREPARATION OF INTERMEDIATES

The following examples illustrate intermediates useful in the preparation of compounds according to the invention:

Example I
Preparation of 2-(2-methylthioethoxy)nitrobenzene 2-methylthioethylchloride (18.0 g, 0.16 mole), o-nitrophenol (20.8 g, 0.15 mole) and potassium carbonate (24.7 g, 0.18 mole) was refluxed in acetonitrile for 24 h. The reaction mixture was filtered and the solvent was evaporated. The residue was dissolved in methylene chloride and washed with water once and thereafter twice with a saturated sodium carbonate solution. The organic layer was dried over sodium sulfate and the solvent was evaporated giving 20.2 g (63%) of the title compound as an oily residue.

($^1$H-NMR, 300 MHz, CDCl$_3$), 2.21 (s,3H), 2.90 (t,2H), 4.27 (t,2H), 7.04 (m,2H), 7.50 (m,1H), 7.79 (m,1H).

Example II
Preparation of 2-(2-methylthioethoxy)aniline

Tin chloride dihydrate (57.9 g, 0.26 mole) in ethyl alcohol (90 ml) was added to a mixture of 2-(2-methylthioethoxy)nitrobenzene (18.1g, 0.085 mole), conc. HCl (72.4 ml) and ethyl alcohol (36 ml). The reaction mixture was stirred for 24 h at room temperature. Sodium hydroxide (6M, 270 ml) was added to the reaction mixture. Extraction with methylene chloride (3×400 ml) gave after drying the organic layer over sodium sulfate and evaporation of the solvent 14.8 g (95%) of the title compound.

($^1$H-NMR, 300 MHz, CDCl$_3$), 2.28 (s,3H), 2.90 (t,2H), 4.18 (t,2H), 4.83 (b,2H), 6.66–6.83 (m,4H).

Example III
Preparation of ethyl 2-butyl-3-(2-(2-methylthioethoxy) phenylamino) acrylate A mixture of 2-(2-methylthioethoxy)aniline (1.6 g, 8.7 mmol), ethyl butyryl acetate (1.38 g, 8.7 mmol) and triethyl orthoformate (1.30 g, 8.8 mmol) was heated to 120° C. for 1 h and ethyl alcohol was distilled off. The reaction mixture was cooled to room temperature. Trituration with methyl alcohol gave 1.08 g (35%) of the desired compound as a solid.

($^1$H-NMR, 300 MHz, CDCl$_3$) 0.96 (t,3H), 1.33 (t,3H), 1.68 (m,3H), 2.22 (s,3H), 2.92 (t,2H), 3.00 (t,2H), 4.25 (m,4H), 6.9–7.3 (m,4H), 8.5 (d,1H), 12.81 (d,1H).

Example IV
Preparation of 3-butyryl-8-(2-methylthioethoxy)-4(1H)-quinolone

Ethyl 2-butyryl-4-(2-(2-methylthioethoxy)phenylamino) acrylate (1.07, 3.04 mmol) was added to refluxing diphenyl ether. The mixture was refluxed for 50 min. The reaction mixture was cooled to room temperature. Petroleum ether was added (70 ml) and after stirring the mixture for further 90 min, the precipitate was filtered off giving 0.8 g (85%) of the title compound.

($^1$H-NMR, 500 MHz, CDCl$_3$), 1.02 (t,3H), 1.75 (m,2H), 2.22 (s,3H), 3.00 (t,2H), 3.25 (t,2H), 4.36 (t,2H), 7.15 (d,1H), 7.35 (m,1H), 8.06 (d,1H), 8.58 (s,1H), 9.40 (b,1H).

Example V
Preparation of 3-butyryl-4-chloro-8-(2-methylthioethoxy)-quinolone 3-butyryl-8-(2-methylthioethoxy)-4(1H)-quinolone (0.8 g, 2.8 mmol) and phosphorus oxychloride (10 ml) was stirred at room temperature for 1 h. The phosphorus oxychloride was evaporated. The residue was partitioned between water and methylene chloride. pH was adjusted to 8 with sodium bicarbonate. The organic layer was dried over sodium sulfate and the solvent was evaporated giving 0.57 g (68%) of the desired compound.

($^1$H-NMR, 300 MHz, CDCl$_3$), 0.97 (t,3H), 1.86 (m,2H), 2.22 (s,3H), 3.00 (t,2H), 3.05 (t,2H), 4.38 (t,2H), 7.16 (d,1H), 7.57 (m,1H), 7.87 (d,1H), 8.84 (s,1H).

Example VI
Preparation of 3-propanoyl-4-chloro-8-(2-methyl thioethoxy)-quinoline The title compound was prepared according to the method in Example V Yield: 0.6 g (75%).

($^1$H-NMR, 300 MHz, CDCl$_3$) 1.26 (t,3H), 2.26 (s,3H), 3.01–3.07 (m,4H), 4.39 (t,2H), 7.15 (d,1H), 7.55 (m,1H), 7.85 (d,1H), 8.84 (s,1H).

Example VII
Preparation of 3-propanoyl-4-chloro-8-(2-propylthioethoxy)-quinoline.

3-Propanoyl-4-chloro-8-(2-propylthioethoxy) quinoline was synthesized according to Example V. Yield 2.5 g (88%).

($^1$H-NMR, 300 MHz, CDCl$_3$) 0.97 (t, 3H), 1.23 (t, 3H), 1.62 (m, 2H), 2.61 (t, 2H), 3.00–3.09 (m, 4H), 4.36 (t, 2H), 7.15 (d, 1H), 7.57 (t, 1H), 7.87 (d, 1H), 8.85 (s, 1H).

Example VIII
Preparation of 3-propanoyl-4-chloro-8-(2-propylthiopropoxy)-quinoline 3-Propanoyl-4-chloro-8-(3-propylthiopropoxy) quinoline was synthesized according to example V Yield 5.5 g (87%).

($^1$H-NMR, 300 MHz, CDCl$_3$) 0.90 (t, 3H), 1.20 (t, 3H), 1.54 (m, 2H), 2.22 (m, 2H), 2.44 (t, 2H), 2.72 (t, 2H), 3.00 (q, 2H), 4.30 (t, 2H), 7.14 (d, 1H), 7.53 (t, 1H), 7,81 (d, 1H), 8,83 (s, 1H).

Example IX
Preparation of 3-butyryl-4-chloro-8-(3-methylthiopropoxy)-quinoline The title compound was synthesized according to the method in Example V. Yield 2.9 g (91%) (hydrochloride).

($^1$H-NMR, 500 MHz, CDCl$_3$) 1.02 (t, 3H), 1.8 (m, 2H), 2.30 (s, 3H), 2.40 (m, 2H), 2.90 (t, 2H), 3.10 (t, 2H), 4.50 (t, 2H), 7.52 (d, 1H), 7.90–7.95 (m, 1H), 8.30–8.50 (m, 1H), 9.48 (s, 1H).

Example X
Preparation of 3-propanoyl-4-chloro-8-(3-methylthiopropoxy)quinoline The title compound was synthesized according to the method in Example V. Yield 3.95 g (96%).

($^1$H-NMR, 300 MHz, CDCl$_3$) 1.28 (t,3H), 2.1 (s, 3H), 2.3 (q, 2H), 2.8 (t, 2H), 3.08 (q, 2H), 4.38 (t,2H), 7.23 (d, 1H), 7.6 (t, 1H), 7.9 (d, 1H), 8.9 (s, 1H).

3. PREPARATION OF PHARMACEUTICAL FORMULATIONS

Pharmaceutical formulations containing a compound of the invention as active ingredient are illustrated in the following examples:

Formulation A. Syrup

A syrup containing 1% (weight per volume) of active substance is prepared from the following ingredients:

| | |
|---|---|
| Compound according to Example 2 | 1.0 g |
| Sugar, powder | 30.0 g |
| Saccharine | 0.6 g |
| Glycerol | 5.0 g |
| Flavouring agent | 0.05 g |
| Ethanol 96% | 5.0 g |
| Distilled water q.s. to a final volume of | 100 ml |

Sugar and saccharine are dissolved in 60 g of warm water. After cooling the acid addition salt is dissolved in the sugar solution and glycerol and a solution of flavouring agents dissolved in ethanol are added. The mixture is diluted with water to a final volume of 100 ml.

The above given active substance may be replaced with other pharmaceutically acceptable acid addition salts.

Formulation B. Tablets

A tablet containing 50 mg of active compound is prepared from the following ingredients:

| I  | Compound according to Example 2   | 500 g |
|----|-----------------------------------|-------|
|    | Lactose                           | 700 g |
|    | Methyl cellulose                  | 6 g   |
|    | Polyvinylpyrrolidone cross-linked | 50 g  |
|    | Magnesium stearate                | 15 g  |
|    | Sodium carbonate                  | 6 g   |
|    | Distilled water                   | q.s.  |
| II | Hydroxypropyl methylcellulose     | 36 g  |
|    | Polyethylene glycol               | 9 g   |
|    | Colour Titanium dioxide           | 4 g   |
|    | Purified water                    | 313 g |

I. Compound according to Example 2, powder, is mixed with lactose and granulated with a water solution of methyl cellulose and sodium carbonate. The wet is forced through a sieve and the granulate dried in an oven. After drying, the granulate is mixed with polyvinylpyrrolidone and magnesium stearate. The dry mixture is pressed into tablet cores (10,000 tablets), each tablet containing 50 mg of active substance, in a tabletting machine using 7 mm diameter punches.

II. A solution of hydroxypropyl methylcellulose and polyethylene glycol in purified water is prepared. After dispersion of titanium dioxide the solution is sprayed onto the tablets I in an Accela Cota®, Manesty coating equipment. A final tablet weight of 130 mg is obtained.

Formulation C. Solution for intravenous administration

A parenteral formulation for intravenous use, containing 4 mg of active compound per ml, is prepared from the following ingredients:

| Compound according to Example 2       | 4 g       |
|---------------------------------------|-----------|
| Polyethylene glycol 400 for injection | 400 g     |
| Disodium hydrogen phosphate           | q.s.      |
| Sterile water to a final volume of    | 1.000 ml  |

Compound according to Example 2 is dissolved in polyethylene glycol 400 and 550 ml of water is added. pH of the solution is brought to pH 7.4 by adding a water solution of disodium hydrogen phosphate and water is added to a final volume of 1000 ml. The solution is filtered through a 0.22 $\mu$m filter and immediately dispensed into 10 ml sterile ampoules. The ampoules are sealed.

4. BIOLOGICAL TESTS

A. Inhibiting effect on acid secretion in vitro in isolated rabbit gastric glands was measured as described by Berglindh et al. (1976) Acta Physiol. Scand. 97, 401–414. The compounds according to Examples 1–12 had an $IC_{50}$ value in the range of 0.5 to 6.0 $\mu$M. The compounds according to Examples 13–57 had an $IC_{50}$ value in the range of 0.75 to 14 $\mu$M B. Inhibiting effect on acid secretion in vivo in conscious female rats was measured according to the following method:

Female rats of the Sprague-Dawly strain were used. They were equipped with cannulated fistulae in the stomach (lumen) and the upper part of the duodenum, for collection of gastric secretions and administration of test substances, respectively. A fourteen days recovery period after surgery was allowed before testing commenced.

Before secretory tests, the animals were deprived of food but not water for 20 h. The stomach was repeatedly washed through the gastric cannula with tap water (37° C.), and 6 ml of Ringer-Glucose given subcutaneously Acid secretion was stimulated with infusion during 3 h (1.2 ml/h, subcutaneously) of pentagastrin and carbachol (20 and 110 mmol/kg h, respectively), during which time gastric secretions were collected in 30-min fractions. Test substances or vehicles were given intravenously or intraduodenally at 60 min after starting the stimulation, in a volume of 1.2 ml/h. Gastric juice samples were titrated to pH 7.0 with NaOH, 0.1 mole/L, and acid output calculated as the product of titrant volume and concentration.

Further calculations were based on group mean responses from 4–5 rats. The acid output during the periods after administration of test substances or vehicle were expressed as fractional responses, setting the acid output in the 30-min period preceding administration to 1.0. Percentage inhibition was calculated from the fractional responses elicited by test compound and vehicle. $ED_{50}$ values were obtained from graphical interpolation on log dose-response curves, or estimated form single-dose experiments assuming a similar slope for all dose-response curves.

The compounds 1–12 in Table 1 had an $ED_{50}$ value in the range of 1.0–12 $\mu$mole/kg. The results are based on gastric acid secretion during the second hour after drug/vehicle administration.

I claim:

1. A compound of the general formula III

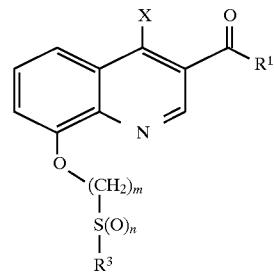

wherein $R^1$ represents $C_1$–$C_6$ alkyl; $R^3$ represents $C_1$–$C_6$ alkyl; m represents 2 or 3; n represents 0, 1 or 2; and X is a leaving group.

2. A process for the preparation of a compound of the general formula I,

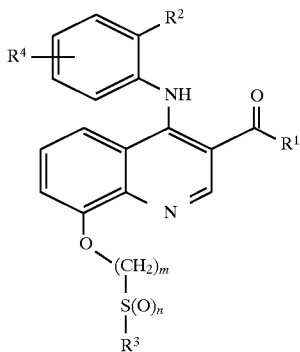

or a pharmaceutically acceptable salt of said compound, wherein $R^1$ is
 (a) $C_1$–$C_6$ alkyl,
 (b) $C_3$–$C_6$ cycloalkyl, or (c) $C_3$–$C_6$, $C_1$–$C_6$ cycloalkylalkyl;

$R^1$ is
- (a) H,
- (b) $C_1$–$C_6$ alkyl,
- (c) $C_1$–$C_6$ alkoxy, or
- (d) halogen;

$R^3$ is $C_1$–$C_6$ alkyl;

$R^4$ is
- (a) H,
- (b) $C_1$–$C_4$ alkyl,
- (c) halogen, or
- (d) OH;

m is an integer 2 or 3; and n is an integer 0, 1 or 2, comprising
(a) reacting a compound of the general formula II

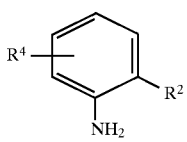

wherein $R^2$ and $R^4$ are defined as above with a compound of the general formula III

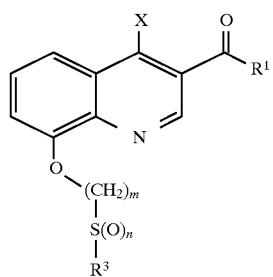

wherein $R^1$, $R^3$, m and n are as defined above and X is a leaving group, or (b) preparing a compound of the formula I wherein $R^1$, $R^2$, $R^3$, $R^4$ and m are as defined above and n is 1 or 2, by oxidizing a compound of formula I wherein $R^1$, $R^2$, $R^3$, $R^4$ and m are as defined above and n is 0.

3. A process according to claim 2, wherein the said oxidation step is performed by (i) using an oxidation agent, whereby oxidation takes place in a solvent such as halogenated hydrocarbons, alcohols, ethers or ketones; or (ii) carrying out the oxidation enzymatically by using an oxidizing enzyme; or (iii) carrying out the oxidation microbiotically by using a suitable microorganism.

4. The process according to claim 2, wherein in the general formula I, $R^1$, is $CH_3$, $CH_2CH_3$, $CH_2CH_2CH_3$, $CH(CH_3)_2$, cylcopropyl or cyclopropylmethyl, $R^2$ is $CH_3$, $CH_2CH_3$, $CH_2CH_2CH_3$, $CH(CH_3)_2$, $CH(CH_3)$ $CH_2CH_3$, $OCH_3$, $OCH_2CH_3$, or halogen, $R^3$ is $CH_3$, $CH_2CH_3$, $CH(CH_3)_2$, or $CH_2CH_2CH_3$; and $R^4$ is H, $CH_3$, $CH_2CH_3$, halogen or OH.

5. The process according to claim 2, wherein in the general formula I, $R^1$, is $CH_2CH_3$ or $CH_2CH_2CH_3$, $R^2$ is $CH_3$, $CH_2CH_3$, $CH(CH_3)_2$, $OCH_3$, or Cl;

$R^3$ is $CH_3$, $CH_2CH_2$, or $CH_2CH_2CH_3$; and $R^4$ is H, $CH_3$, F, Cl or OH.

6. The process according to claim 2, wherein the compound is one as listed in the Table below, or a pharmaceutically acceptable salt thereof,

| No. | $R^1$ | $R^2$ | $R^3$ | $R^4$ | m | n |
|---|---|---|---|---|---|---|
| 1 | $C_2CH_2CH_3$ | $CH_3$ | $CH_3$ | H | 2 | 0 |
| 2 | $CH_2CH_2CH_3$ | $CH_3$ | $CH_3$ | H | 2 | 1 |
| 3 | $CH_2CH_2CH_3$ | $CH_3$ | $CH_3$ | H | 2 | 2 |
| 4 | $CH_2CH_2CH_3$ | $CH(CH_3)_2$ | $CH_3$ | H | 2 | 0 |
| 5 | $CH_2CH_2CH_3$ | $CH(CH_3)_2$ | $CH_3$ | H | 2 | 1 |
| 6 | $CH_2CH_2CH_3$ | $CH(CH_3)_2$ | $CH_3$ | H | 2 | 2 |
| 7 | $CH_2CH_3$ | $CH_3$ | $CH_3$ | H | 2 | 0 |
| 8 | $CH_2CH_3$ | $CH_3$ | $CH_3$ | H | 2 | 1 |
| 9 | $CH_2CH_3$ | $CH_3$ | $CH_3$ | H | 2 | 2 |
| 10 | $CH_2CH_3$ | $CH_2CH_3$ | $CH_3$ | H | 2 | 0 |
| 11 | $CH_2CH_3$ | $CH_2CH_3$ | $CH_3$ | H | 2 | 1 |
| 12 | $CH_2CH_3$ | $CH_2CH_3$ | $CH_3$ | H | 2 | 2 |
| 13 | $CH_2CH_2CH_3$ | $CH_3$ | $CH_3$ | 4-F | 2 | 0 |
| 14 | $CH_2CH_2CH_3$ | $CH_3$ | $CH_3$ | 4-F | 2 | 1 |
| 15 | $CH_2CH_2CH_3$ | $CH_3$ | $CH_3$ | 4-F | 2 | 2 |
| 16 | $CH_2CH_3$ | $CH(CH_3)_2$ | $CH_3$ | H | 2 | 0 |
| 17 | $CH_2CH_2CH_3$ | $CH_2CH_3$ | $CH_3$ | H | 2 | 0 |
| 18 | $CH_2CH_2CH_3$ | $CH_2CH_3$ | $CH_3$ | H | 2 | 1 |
| 19 | $CH_2CH_2CH_3$ | $CH_2CH_3$ | $CH_3$ | H | 2 | 2 |
| 20 | $CH_2CH_3$ | $CH_3$ | $CH_2CH_2CH_3$ | H | 2 | 0 |
| 21 | $CH_2CH_3$ | $CH_3$ | $CH_2CH_2CH_3$ | H | 2 | 1 |
| 22 | $CH_2CH_3$ | $CH_3$ | $CH_2CH_2CH_3$ | H | 2 | 2 |
| 23 | $CH_2CH_3$ | $CH_3$ | $CH_2CH_2CH_3$ | H | 3 | 0 |
| 24 | $CH_2CH_3$ | $CH_3$ | $CH_2CH_2CH_3$ | H | 3 | 1 |
| 25 | $CH_2CH_3$ | $CH_3$ | $CH_2CH_2CH_3$ | H | 3 | 2 |
| 26 | $CH_2CH_2CH_3$ | $CH_3$ | $CH_3$ | 4-OH | 2 | 0 |
| 27 | $CH_2CH_2CH_3$ | $CH_3$ | $CH_3$ | 4-OH | 2 | 1 |
| 28 | $CH_2CH_2CH_3$ | $CH_3$ | $CH_3$ | 4-OH | 2 | 2 |
| 29 | $CH_2CH_2CH_3$ | Cl | $CH_3$ | H | 2 | 0 |
| 30 | $CH_2CH_2CH_3$ | Cl | $CH_3$ | H | 2 | 1 |
| 31 | $CH_2CH_2CH_3$ | Cl | $CH_3$ | H | 2 | 2 |
| 32 | $CH_2CH_2CH_3$ | $OCH_3$ | $CH_3$ | H | 2 | 0 |
| 33 | $CH_2CH_2CH_3$ | $OCH_3$ | $CH_3$ | H | 2 | 1 |
| 34 | $CH_2CH_2CH_3$ | $OCH_3$ | $CH_3$ | H | 2 | 2 |
| 35 | $CH_2CH_2CH_3$ | $CH_3$ | $CH_3$ | 4-$CH_3$ | 2 | 0 |
| 36 | $CH_2CH_2CH_3$ | $CH_3$ | $CH_3$ | 4-$CH_3$ | 2 | 1 |
| 37 | $CH_2CH_2CH_3$ | $CH_3$ | $CH_3$ | 4-$CH_3$ | 2 | 2 |
| 38 | $CH_2CH_2CH_3$ | $CH_3$ | $CH_3$ | 6-$CH_3$ | 2 | 0 |
| 39 | $CH_2CH_2CH_3$ | $CH_3$ | $CH_3$ | 6-$CH_3$ | 2 | 1 |
| 40 | $CH_2CH_2CH_3$ | $CH_3$ | $CH_3$ | 6-$CH_3$ | 2 | 2 |
| 41 | $CH_2CH_2CH_3$ | $CH_3$ | $CH_3$ | 6-Cl | 2 | 0 |
| 42 | $CH_2CH_2CH_3$ | $CH_3$ | $CH_3$ | 6-Cl | 2 | 1 |
| 43 | $CH_2CH_2CH_3$ | $CH_3$ | $CH_3$ | 6-Cl | 2 | 2 |
| 44 | $CH_2CH_3$ | $CH_3$ | $CH_3$ | H | 3 | 0 |
| 45 | $CH_2CH_3$ | $CH_3$ | $CH_3$ | H | 3 | 1 |
| 46 | $CH_2CH_3$ | $CH_3$ | $CH_3$ | H | 3 | 2 |
| 47 | $CH_2CH_2CH_3$ | Cl | $CH_3$ | H | 3 | 0 |
| 48 | $CH_2CH_2CH_3$ | Cl | $CH_3$ | H | 3 | 1 |
| 49 | $CH_2CH_2CH_3$ | Cl | $CH_3$ | H | 3 | 2 |
| 50 | $CH_2CH_2CH_3$ | $CH_3$ | $CH_3$ | H | 3 | 0 |
| 51 | $CH_2CH_2CH_3$ | $CH_3$ | $CH_3$ | H | 3 | 1 |
| 52 | $CH_2CH_2CH_3$ | $CH_3$ | $CH_3$ | H | 3 | 2 |
| 53 | $CH_2CH_2CH_3$ | $CH_3$ | $CH_3$ | H | 3 | 0 |
| 54 | $CH_2CH_2CH_3$ | $OCH_3$ | $CH_3$ | H | 3 | 1 |
| 55 | $CH_2CH_2CH_3$ | $OCH_3$ | $CH_3$ | H | 3 | 2 |

7. The process claim according to claim 2 wherein the compound is 3-butyryl-4-(2-methylphenylamino)-8-(2-methylsulfinyl-ethoxy)quinoline or a pharmaceutical thereof.

8. A method for the treatment or prophyluris of conditions involving infection by *Helicobacter pylori* of human gastric nucosa, which comprises administering to a mammal, in need of such treatment an effective amount of a compound of the general formula I

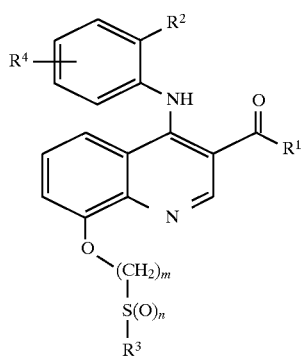

or a pharmaceutically acceptable salt of the said compound,
wherein $R^1$ is
 (a) $C_1$–$C_6$ alkyl,
 (b) $C_3$–$C_6$ cycloalkyl, or
 (c) $C_3$–$C_6$, $C_1$–$C_6$ cycloalkylalkyl;
$R^2$ is
 (a) H,
 (b) $C_1$–$C_6$ alkyl,
 (c) $C_1$–$C_6$ alkoxy, or
 (d) halogen;
$R^3$ is $C_1$–$C_6$ alkyl;
$R^4$ is
 (a) H,
 (b) $C_1$–$C_4$ alkyl,
 (c) halogen, or
 (d) OH;
m is an integer 2 or 3; and
n is an integer 0, 1 or 2,
wherein the compound or pharmaceutically acceptable salt is administered in combination with at least one antimicrobial agent.

9. A pharmaceutical formulation for the treatment or prophylaxis of conditions involving infection by *Helicobacter pylori* of human gastric mucosa, comprising as the active ingredient a compound of the general formula I, or a pharmaceutically acceptable salt thereof, in combination with at least one antimicrobial agent and a pharmaceutically acceptable carrier, wherein the compound of the formula I has the following structure

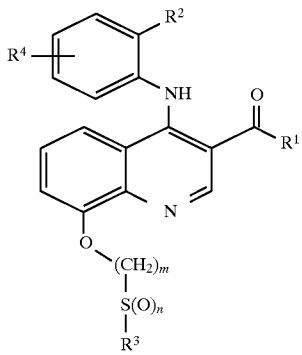

wherein $R^1$ is
 (a) $C_1$–$C_6$ alkyl,
 (b) $C_3$–$C_6$ cycloalkyl, or
 (c) $C_3$–$C_6$, $C_1$–$C_6$ cycloalkylalkyl;
$R^2$ is
 (a) H,
 (b) $C_1$–$C_6$ alkyl,
 (c) $C_3$–$C_6$ alkoxy, or
 (d) halogen;
$R^3$ is $C_1$–$C_6$ alkyl;
$R^4$ is
 (a) H,
 (b) $C_1$–$C_4$ alkyl,
 (c) halogen, or
 (d) OH;
m is an integer 2 or 3; and
n is an integer 0, 1 or 2.

10. The method according to claim 8 wherein the compound is 3-butyryl-4-(2-methyl-phenylamino)-8-(2-methylsulfinylethoxy)quinoline or a pharmaceutical salt thereof.

* * * * *

UNITED STATES PATENT AND TRADEMARK OFFICE
CERTIFICATE OF CORRECTION

PATENT NO. : 5,889,021

DATED : March 30, 1999

INVENTOR(S) : Carl Ingemar Starke

It is certified that error appears in the above-identified patent and that said Letters Patent is hereby corrected as shown below:

In claim 8, column 26, line 62, delete "prophyluris" and substitute therefore -- prophylaxis --, and at line 64, delete "nucosa" and substitute therefor -- mucosa --.

In claim 9, column 28, line 26, delete "$C_3 - C_6$ alkoxy" and substitute therefor -- $C_1 - C_6$ alkoxy --.

Signed and Sealed this

Twenty-fourth Day of August, 1999

Attest:

Attesting Officer

Q. TODD DICKINSON

Acting Commissioner of Patents and Trademarks